(12) United States Patent
Cros et al.

(10) Patent No.: US 11,033,192 B2
(45) Date of Patent: Jun. 15, 2021

(54) WIRELESS SENSOR FOR MEASURING PRESSURE

(71) Applicant: ST. JUDE MEDICALLUXEMBOURG HOLDINGS II S.A.R.L. ("SJM LUX 11"), Luxembourg (LU)

(72) Inventors: Florent Cros, Decatur, GA (US); David O'Brien, Atlanta, GA (US); Michael Fonseca, Marietta, GA (US); Matthew Abercrombie, Marietta, GA (US); Jin Woo Park, Suwanee, GA (US); Angad Singh, Marietta, GA (US)

(73) Assignee: ST. JUDE MEDICAL LUXEMBOURG HOLDINGS II S.A.R.L. ("SJM LUX 11"), Luxembourg (LU)

( * ) Notice: Subject to any disclaimer, the term of this patent is extended or adjusted under 35 U.S.C. 154(b) by 319 days.

(21) Appl. No.: 16/194,103

(22) Filed: Nov. 16, 2018

(65) Prior Publication Data
US 2019/0099087 A1    Apr. 4, 2019

Related U.S. Application Data

(60) Continuation of application No. 14/733,450, filed on Jun. 8, 2015, now Pat. No. 10,143,388, which is a
(Continued)

(51) Int. Cl.
*A61N 1/365*    (2006.01)
*A61B 5/0215*    (2006.01)
(Continued)

(52) U.S. Cl.
CPC ........ *A61B 5/0215* (2013.01); *A61B 5/02055* (2013.01); *A61B 5/6882* (2013.01);
(Continued)

(58) Field of Classification Search
CPC .............. A61B 5/0215; A61B 5/02014; A61B 5/02055; A61B 5/0031; A61B 5/076; A61B 5/6882; H05K 3/32
See application file for complete search history.

(56) References Cited

U.S. PATENT DOCUMENTS

| | | | | |
|---|---|---|---|---|
| 4,701,826 A | * | 10/1987 | Mikkor | ................. G01L 9/0073 361/283.4 |
| 5,994,638 A | * | 11/1999 | Edelson | ................. H01J 45/00 136/205 |

(Continued)

*Primary Examiner* — Paul D Kim
(74) *Attorney, Agent, or Firm* — The Small Patent Law Group LLC; Dean D. Small

(57) ABSTRACT

A pressure sensor is provided that comprises an upper wafer formed from a dielectric material, the upper wafer having channels. The upper wafer includes a first capacitor plate and a second capacitor plate formed on a lower surface of the upper wafer. An inductor is contained within the channels in the upper wafer in fixed relation to the first and second capacitor plates. A lower wafer is formed from the dielectric material. A third capacitor plate is formed on an inner surface of the lower wafer. The upper and lower wafers are fused together to form a monolithic housing such that the first and second capacitor plates are arranged in parallel, spaced-apart relation from the third capacitor plate. The lower wafer comprising a pressure sensitive deflective (Continued)

region underlying the third capacitor plate. The deflective region deflects in response to changes in ambient pressure in the medium.

14 Claims, 16 Drawing Sheets

Related U.S. Application Data continuation of application No. 12/612,070, filed on Nov. 4, 2009, now Pat. No. 9,078,563, which is a division of application No. 11/204,812, filed on Aug. 16, 2005, now Pat. No. 7,621,036, which is a continuation-in-part of application No. 11/157,375, filed on Jun. 21, 2005, now abandoned.

(51) Int. Cl.
*H05K 3/32* (2006.01)
*A61B 5/0205* (2006.01)
*A61B 5/00* (2006.01)

(52) U.S. Cl.
CPC ........ *H05K 3/32* (2013.01); *A61B 2562/0247* (2013.01); *A61B 2562/12* (2013.01); *A61N 1/36564* (2013.01); *Y10T 29/4913* (2015.01); *Y10T 29/49117* (2015.01)

(56) References Cited

U.S. PATENT DOCUMENTS

| | | | | |
|---|---|---|---|---|
| 6,919,240 | B2* | 7/2005 | Uzawa | H01G 9/10 438/171 |
| 6,939,299 | B1* | 9/2005 | Petersen | A61B 3/16 600/300 |
| 7,574,792 | B2* | 8/2009 | O'Brien | A61B 5/0031 29/600 |
| 7,647,836 | B2* | 1/2010 | O'Brien | G01L 9/0042 73/756 |
| 8,025,625 | B2* | 9/2011 | Allen | A61B 5/021 600/561 |
| 9,265,428 | B2* | 2/2016 | O'Brien | A61B 5/076 |
| 2005/0124896 | A1* | 6/2005 | Richter | A61B 5/0215 600/458 |
| 2006/0174712 | A1* | 8/2006 | O'Brien | G01L 9/0075 73/756 |
| 2006/0177956 | A1* | 8/2006 | O'Brien | B81C 1/00301 438/50 |
| 2006/0235310 | A1* | 10/2006 | O'Brien | A61B 5/0031 600/486 |
| 2006/0241354 | A1* | 10/2006 | Allen | A61B 5/021 600/300 |
| 2009/0030291 | A1* | 1/2009 | O'Brien | A61B 5/02014 600/301 |
| 2009/0278553 | A1* | 11/2009 | Kroh | A61B 5/05 324/633 |
| 2010/0022896 | A1* | 1/2010 | Yadav | A61B 5/05 600/488 |

* cited by examiner

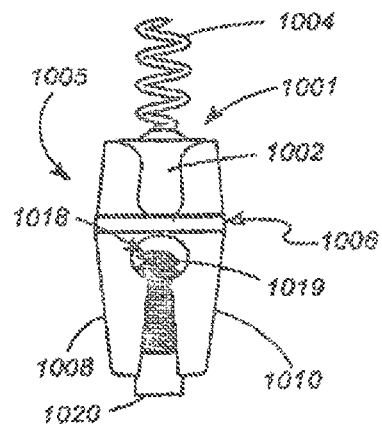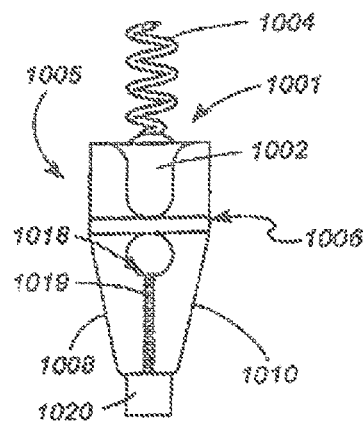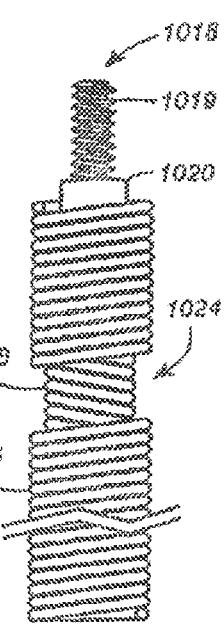
Fig. 33　　　Fig. 34　　　Fig. 37
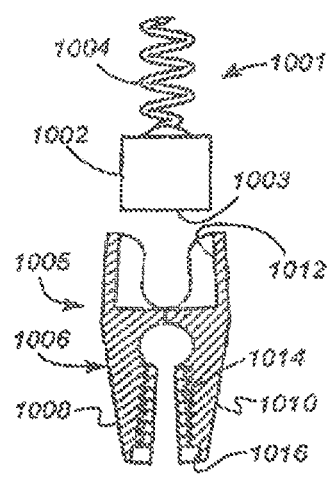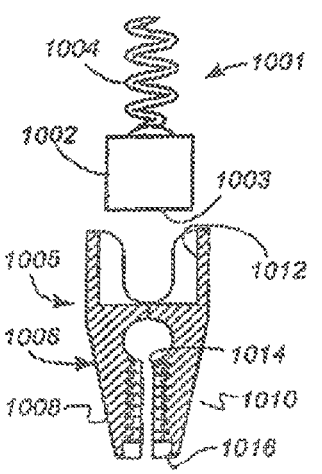
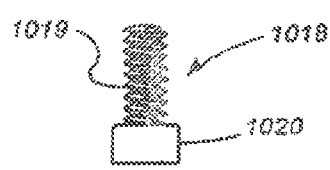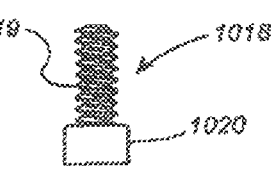
Fig. 35　　　Fig. 36

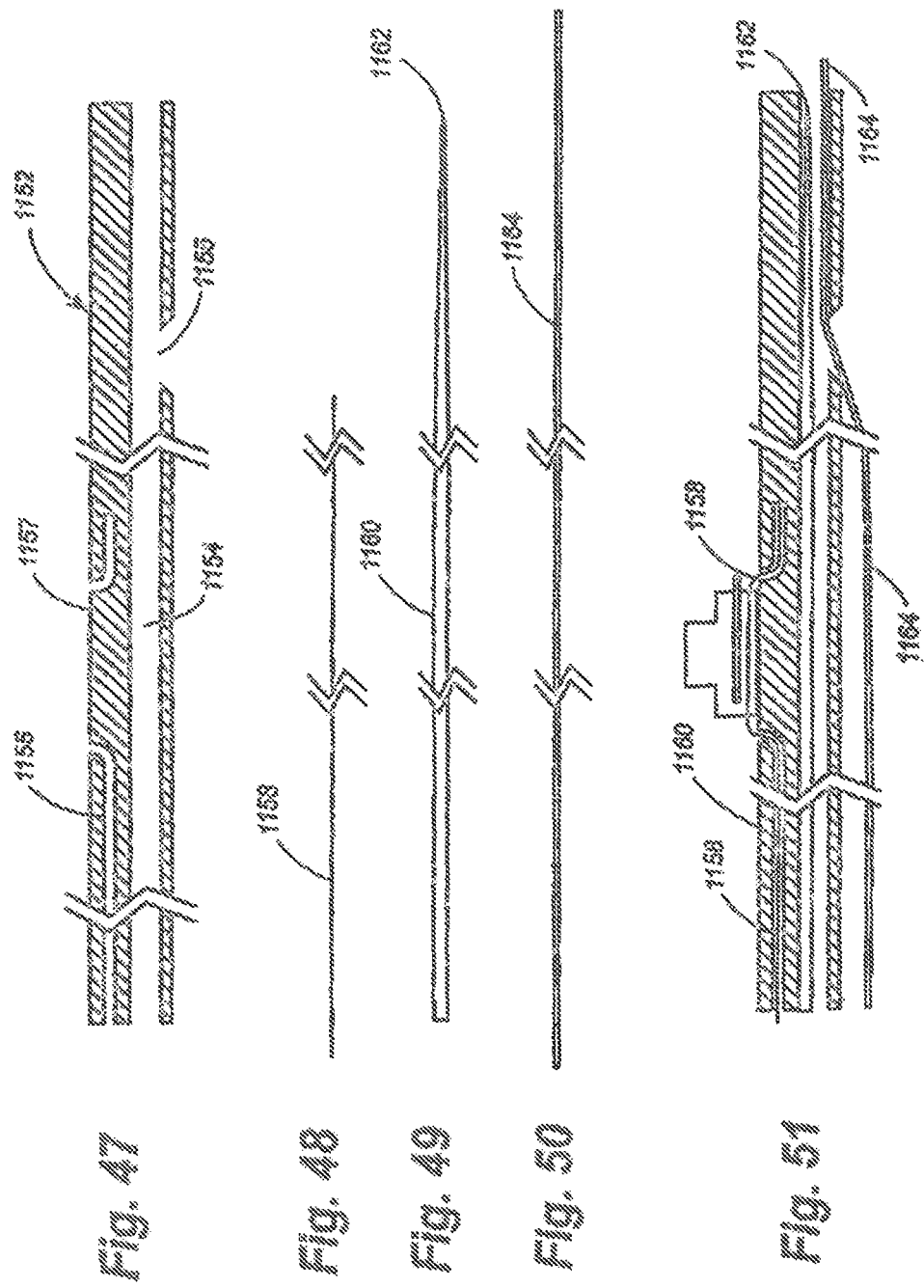

WIRELESS SENSOR FOR MEASURING PRESSURE

CROSS-REFERENCE TO RELATED APPLICATION

This application is a continuation of U.S. patent application Ser. No. 14/733,450, filed Jun. 8, 2015 and entitled "Method of Manufacturing Implantable Wireless Sensor for in Vivo Pressure Measurement which is a continuation of U.S. patent application Ser. No. 12/812,070, filed Nov. 4, 2009 and entitled "Method of Manufacturing Implantable Wireless Sensor for In Vivo Pressure Measurement," now U.S. Pat. No. 9,078,583 which is a divisional of U.S. patent application Ser. No. 11/204,812, filed on Aug. 18, 2005 and entitled "Method of Manufacturing Implantable Wireless Sensor for In Vivo Pressure Measurement," now U.S. Pat. No. 7,821,038; which, in turn, is a continuation-in-part of U.S. patent application Ser. No. 11/157,375, filed Jun. 21, 2005 and entitled "Implantable Wireless Sensor for In Vivo Pressure Measurement," the disclosures of which are hereby incorporated by reference in their entirety" to—This application is a continuation of U.S. patent application Ser. No. 14/733,450, filed Jun. 8, 2015 and entitled "Method of Manufacturing Implantable Wireless Sensor for In Vivo Pressure Measurement, now U.S. Pat. No. 10,143,388, which is a continuation of U.S. patent application Ser. No. 12/812,070, filed Nov. 4, 2009 and entitled "Method of Manufacturing Implantable Wireless Sensor for In Vivo Pressure Measurement," now U.S. Pat. No. 9,078,583 which is a divisional of U.S. patent application Ser. No. 11/204, 812, filed on Aug. 18, 2005 and entitled "Method of Manufacturing Implantable Wireless Sensor for In Vivo Pressure Measurement," now U.S. Pat. No. 7,821,038; which, in turn, is a continuation-in-part of U.S. patent application Ser. No. 11/157,375, filed Jun. 21, 2005 and entitled "Implantable Wireless Sensor for In Vivo Pressure Measurement", now abandoned, which are hereby incorporated by reference in theft entirety.

TECHNICAL HELD

This invention relates to methods of manufacturing implanted sensors for wirelessly sensing pressure, temperature and other physical properties within the human body. More particularly, the invention concerns a method of manufacturing a wireless, un-powered, micromachined pressure sensor that can be delivered using catheter-based endovascular or surgical techniques to a location within an organ or vessel.

BACKGROUND

The measurement of blood pressure within the human heart and its vasculature provides critical information regarding the organ's function. Many methods and techniques have been developed to give physicians the ability to monitor heart function to properly diagnose and treat various diseases and medical conditions. For example, a sensor placed within the chambers of the heart can be used to record variations in blood pressure based on physical changes to a mechanical element within the sensor. This information is then transferred through a wire from the sensor to an extracorporeal device that is capable of translating the data from the sensor into a measurable value that can be displayed. The drawback of this type of sensor is that there must be a wired connection between the sensor and the extracorporeal device, thus limiting Its use to acute settings.

Many types of wireless sensors have been proposed that would allow implantation of the device into the body. Then, through the appropriate coupling means, pressure reading can be made over longer periods of interest. The primary limitation to these type of sensors is that the fabrication methods used to manufacture them do not provide sufficient miniaturization to allow them to be introduced and implanted into the heart using nonsurgical, catheter based techniques while maintaining the ability to communicate wirelessly with external electronics.

An implantable sensor of this type must be assembled using the materials and fabrication methods that ensure appropriate biocompatibility and long term mechanical and electrical durability.

One method of manufacturing a sensor capable of measuring pressure is to use a capacitor that is assembled such that one of the capacitive plates will be displaced with respect to the other as a result of exposure to externally applied stress. This displacement will result in a change in the capacitance that is proportional to the applied stress. Various patents describe the fabrication and use of capacitor-based pressure sensors. The primary limitation of many of these inventions is that the techniques used to fabricate the sensors do not lend themselves to the miniaturization necessary for it to be configured as an implantable medical device while maintaining the capability of communicating wirelessly with external electronics.

The fabrication methodologies that have been developed in the field of Micro-Electro-Mechanical Systems ("MEMS"), however, do specifically provide the means for assembling miniaturized sensors capable of measuring a variety of properties including pressure. MEMS devices as described in prior patents traditionally use silicon as a substrate for construction of miniature electrical or mechanical structures.

A number of patents detail pressure sensors (some capacitive in nature, some manufactured using MEMS based fabrication methods) that are specifically designed for implantation into the human body. These sensors suffer from many of the limitations already mentioned, with the additional concerns that they require either the addition of a power source to operate the device or the need for a physical connection to a device capable of translating the sensor output into a meaningful display of a physiologic parameter.

To overcome the two problems of power and physical connection, the concept of a externally modulated LC circuit has been applied to development of implantable pressure sensors. Of a number of patents that describe a sensor design of this nature, U.S. Pat. No. 6,113,553 to Chubbuck is a representative example. The Chubbuck patent demonstrates how a combination of a pressure sensitive capacitor placed in series with an inductor coil provides the basis for a wireless, un-powered pressure sensor that is suitable for implantation into the human body. Construction of an LC circuit in which variations of resonant frequency correlate to changes in measured pressure and in which these variations can be detected remotely through the use of electromagnetic coupling are further described in U.S. Pat. Nos. 6,111,520 and 6,278,379, both to Allen et al., incorporated herein by reference.

The device described in the Chubbuck patent is large, thus requiring surgical implantation and thereby limiting its applicability to areas that are easily accessible to surgery (e.g., the skull).

Thus, the need exists for a miniature, biocompatible, wireless, un-powered, hermetic pressure sensor that can be delivered into the heart or the vasculature using a small diameter catheter.

SUMMARY

Stated generally, the present invention is directed toward a sensor and method for manufacturing a sensor to measure pressure within the heart or vasculature of a patient. The sensor comprises an upper wafer formed from a dielectric material, the upper wafer having one or more channels. The upper wafer includes a first capacitor plate and a second capacitor plate formed on a lower surface of the upper wafer. According to one embodiment the sensor further comprises an inductor formed from one or more windings of a conductive material, the inductor being contained within the one or more channels in the upper wafer in fixed relation to the first and second capacitor plates, the inductor comprising first and second inductor leads, the first lead being electrically coupled to the first capacitor plate and the second lead electrically coupled to the second capacitor plate. The apparatus further comprises a lower wafer formed from the dielectric material, the lower wafer being thinner than the upper wafer and a third capacitor plate formed on an inner surface of the lower wafer, the upper and lower wafers being fused together to form a monolithic housing such that the first and second capacitor plates are arranged in parallel, spaced-apart relation from the third capacitor plate, a portion of the lower wafer comprising a pressure sensitive deflective region underlying at least a portion of the third capacitor plate, whereby the deflective region deflects in response to changes in ambient pressure in the medium.

Generally the invention further comprises a method for manufacturing a sensor for measuring pressure within the heart or the vasculature of a patient by implanting a pressure sensor in such locations utilizing catheter-based endovascular or surgical techniques and using extracorporeal electronics to measure the pressure easily, safely, and accurately. Stated somewhat more specifically, according to a first aspect of manufacturing a sensor for in vivo applications, a recess is formed in a first wafer, and a capacitor plate is formed in the recess of the first wafer. A second capacitor plate is formed in a corresponding region of a second wafer. The two wafers are mutually imposed and affixed to one another such that the two capacitor plates are arranged in parallel, spaced-apart relation.

According to a second aspect of the invention, a method of manufacturing a sensor for in vivo applications comprises the step of providing three wafers of an electrically non-conductive material. First and second capacitor plates are formed on an upper surface of the first wafer. A third capacitor plate is formed on a lower surface of the second wafer. The first and second wafers are then mutually imposed such that the third capacitor plate is positioned in generally parallel, spaced-apart relation from the first and second capacitor plates. An inductor coil is positioned on top of an upper surface of the second wafer, and the leads of the inductor coil are electrically connected to the first and second capacitor plates. A cavity is formed in the third wafer sufficient to receive said inductor coil, and the third wafer is positioned on top of the second wafer with the inductor coil being received within the cavity of the third wafer. Finally, the second wafer is bonded to the first and third wafers.

According to still another aspect of the invention, a method of manufacturing a sensor for in vivo applications, comprises the steps of forming a bottom plate on a wafer of electrically insulating material, forming a sacrificial layer over the bottom plate, forming a top plate on top of the sacrificial layer, and removing the sacrificial layer to leave the bottom and top plates in spaced-apart relation.

In yet another aspect of the present invention, a method of manufacturing a sensor for in vivo applications includes the step of providing first and second wafers. A recess is formed in the first wafer, and a first plate is formed in the recess of the first wafer. A coil-receiving trench is formed in an upper surface of the second wafer, and second and third plates are formed on the upper surface of the second wafer within the perimeter of the coil-receiving trench. An inductor coil is positioned within the coil-receiving trench in the upper surface of the second wafer, and the leads of the inductor coil are electrically connected to the second and third plates on the upper surface of the second wafer. The first and second wafers are affixed to one another such that the first plate in the recess of the first wafer is in parallel, spaced apart relation to the second and third plates on the upper surface of the second wafer.

Thus it is an object of this invention to provide a method for manufacturing an implantable wireless sensor.

It is also an object of this invention to provide a method for manufacturing a wireless, passive micromechanical sensor that can be delivered endovascularly to a heart chamber or the vasculature.

It is a further object of this invention to provide a method for manufacturing an implantable, wireless, passive sensor that can be delivered endovascularly to a heart chamber or the vasculature to measure pressure and/or temperature.

Other objects, features, and advantages of the present invention will become apparent upon reading the following specification, when taken in conjunction with the drawings and the appended claims.

BRIEF DESCRIPTION OF THE DRAWINGS

FIG. 33 is a side view of a pressure sensor and a retention mechanism of a delivery device, with the retention mechanism in a closed configuration.

FIG. 34 is a side view of the pressure sensor and retention mechanism FIG. 33, with the retention mechanism in an open configuration.

FIG. 35 is a side view of the pressure sensor and retention mechanism FIG. 33, with the retention mechanism in an closed configuration and shown in cross-section.

FIG. 36 is a side view of the pressure sensor and retention mechanism FIG. 33, with the retention mechanism in an open configuration and shown in cross-section.

FIG. 37 is a side view of a dual-coil shaft of a delivery device, with a portion of the outer coil being removed to show the inner coil.

FIG. 47 is a side cutaway view of a shaft of a delivery apparatus for implanting the sensor of FIG. 44.

FIG. 48 is a side view of a tether wire of a delivery apparatus for implanting the sensor of FIG. 44.

FIG. 49 is a side view of a core wire of a delivery apparatus for implanting the sensor of FIG. 44.

FIG. 50 is a side view of a guidewire of a delivery apparatus for implanting the sensor of FIG. 44.

FIG. 51 is a side cutaway view of a delivery apparatus comprising the components of FIGS. 47-50 with the sensor of FIG. 44 mounted thereto.

DETAILED DESCRIPTION

Figure 1:
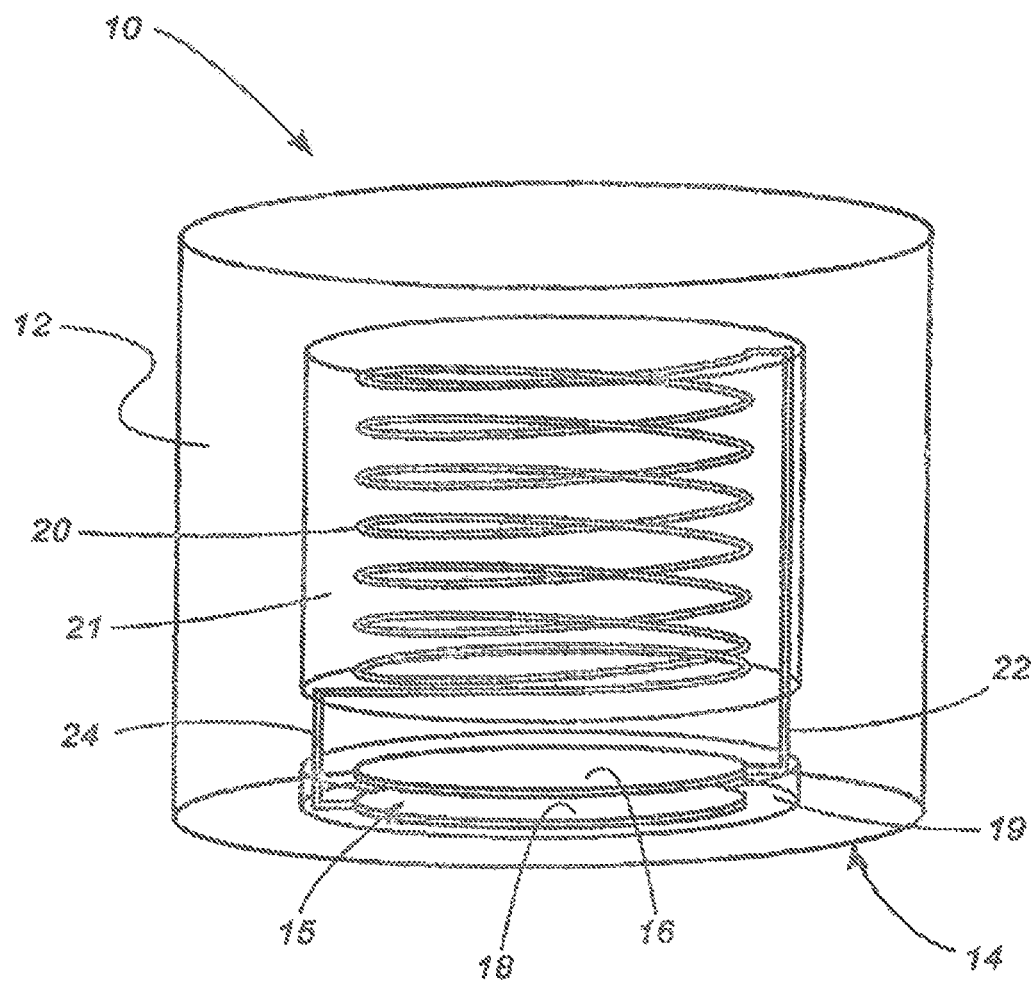
FIG. 1 is a perspective view of a first embodiment of an implantable wireless sensor according to the present invention, with the sensor body shown as transparent to reveal interior detail.

Referring now to the drawings, in which like numerals indicate like elements throughout the several views, FIG. 1 illustrates a sensor 10 for the measurement of physical parameters. The sensor can be fabricated using micro-machining techniques and is small, accurate, precise, durable, robust, biocompatible, and insensitive to changes in body chemistry, or biology. Additionally, the sensor can incorporate radiopaque features to enable fluoroscopic visualization during placement within the body. Furthermore, this sensor is encased in a hermetic, unitary package of electrically insulating material where the package is thinned in one region so as to deform under a physiologically relevant range of pressure. The LC circuit contained in the packaging is configured so that one electrode of the capacitor is formed on the thinned region. This sensor does not require the use of external connections to relay pressure information externally and does not need an internal power supply to perform its function. The pressure sensor of the current invention can be attached to the end of a catheter to be introduced into a human body and delivered to an organ or vessel using catheter-based endovascular techniques.

Referring to FIG. 1, the sensor 10 includes a body 12. The body 12 is formed from electrically insulating materials, preferably biocompatible ceramics. In a preferred embodiment, the body is comprised of fused silica. The sensor 10 comprises a deflectable region 14 at the lower end of the body 12. The body 12 further comprises a lower chamber 19 and an upper chamber 21.

An LC resonator is hermetically housed within the body 12 and comprises a capacitor 16 and an inductor 20. As used herein, the term "hermetic" will be understood to mean "completely sealed, especially against the escape or entry of air and bodily fluids." The capacitor 15 is located within the lower cylindrical chamber 19 and comprises at least two plates 16, 18 disposed in parallel, spaced apart relation. The inductor 20 comprises a coil disposed within the upper chamber 21 and which is in conductive electrical contact with the capacitor 15.

The lower capacitor plate 18 is positioned on the inner surface of the deflectable region 14 of the sensor body 12. The upper capacitor plate 16 is positioned on a fixed region of the sensor body 12. A change in ambient pressure at the deflectable region 14 of the sensor 10 causes the deflectable region 14 to bend, thereby displacing the lower plate 16 with respect to the upper plate 18 and changing the capacitance of the LC circuit. Because the change in capacitance of the LC circuit changes its resonant frequency, the resonant frequency of the sensor 10 is pressure-dependent.

Beyond what has been presented in U.S. Pat. Nos. 6,111,520 and 6,278379, covering the fundamental operating principle of the wireless pressure sensor, additional means to further sensor miniaturization is required in order to achieve an acceptable size for implantation into the heart or the vasculature. The sensor outer dimensions are constrained by the lumen size of the delivery catheter that is used to introduce the sensor. Catheter inner diameters typically range from 1-5 mm. Also, the size and shape of the sensor should minimally interfere with mechanical or hemodynamic function of the heart or vessel where it is located.

Within these physical size constraints, one of the most significant challenges is achieving adequate coupling to the sensor inductor coil from the external readout device at the necessary distance from the outside of the body to the implant site. One method for achieving enhanced coupling is to add magnetic material to the inductor. However, this approach is not feasible in a sensor intended for in vivo use, as the magnetic material would be adverse to magnetic resonance imaging, for example. For a limited coil cross-sectional area, an increased coupling coefficient is also achievable by using a three-dimensional inductor coil configuration, as opposed to two-dimensional designs. For these reasons, a three-dimensional helical inductor coil configuration 20 is the preferred embodiment for the sensor design.

The disclosed sensor features a completely passive inductive-capacitive (LC) resonant circuit with a pressure varying capacitor. Because the sensor is fabricated using completely passive electrical components and has no active circuitry, it does not require on-board power sources such as batteries, nor does it require leads to connect to external circuitry or power sources. These features create a sensor which is self-contained within the packaging material and lacks physical interconnections traversing the hermetic packaging, such interconnects frequently being cited for failure of hermeticity. Furthermore, other sensing capabilities, such as temperature sensing, can be added using the same manufacturing techniques. For example, temperature sensing capability can be accomplished by the addition of a resistor with known temperature characteristics to the basic LC circuit.

The capacitor in the pressure sensor of the disclosed invention consists of at least two conductive elements separated by a gap. If a force is exerted on the sensor, a portion of the sensor deflects, changing the relative position between the at least two conductive elements. This movement will have the effect of reducing the gap between the conductive elements, which will consequently change the capacitance of the LC circuit. An LC circuit is a closed loop system whose resonance is proportional to the inverse square root of the product of the inductor and capacitor. Thus, changes in pressure alter the capacitance and, ultimately, cause a shift in the resonant frequency of the sensor. The pressure of the environment external to the sensor is then determined by referencing the value obtained for the resonant frequency to a previously generated curve relating resonant frequency to pressure.

Because of the presence of the inductor, it is possible to couple to the sensor electromagnetically and to induce a current in the LC circuit via a magnetic loop. This characteristic allows for wireless exchange of electromagnetic energy with the sensor and the ability to operate it without the need for an on-board energy source such as a battery. Thus it is possible to determine the pressure surrounding the sensor by a simple, non-invasive procedure by remotely interrogating the sensor, recording the resonant frequency, and converting this value to a pressure measurement.

One method of sensor interrogation is explained in U.S. patent application Ser. No. 11/105,294, incorporated herein by reference. According to this invention, the interrogating system energizes the sensor with a low duty cycle, gated burst of RF energy having a predetermined frequency or set of frequencies and a predetermined amplitude. The energizing signal is coupled to the sensor via a magnetic loop. The energizing signal induces a current in the sensor that is maximized when the frequency of the energizing signal is substantially the same as the resonant frequency of the sensor. The system receives the ring down response of the sensor via magnetic coupling and determines the resonant frequency of the sensor, which is then used to determine the measured physical parameter. The resonant frequency of the sensor is determined by adjusting the frequency of the energizing signal until the phase of the ring down signal and the phase of a reference signal are equal or at a constant offset. In this manner, the energizing signal frequency is locked to the sensors resonant frequency and the resonant frequency of the sensor is known. The pressure of the localized environment can then be ascertained.

Q factor (Q) is the ratio of energy stored versus energy dissipated. The reason Q is important is that the ring down rate of the sensor is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, it is important to design sensors with values of Q sufficiently high enough to avoid unnecessary increases in complexity in communicating with the sensor via external electronics.

The Q of the sensor is dependent on multiple factors such as the shape, size, diameter, number of turns, spacing between the turns and cross-sectional area of the inductor component. In addition Q will be affected by the materials used to construct the sensors. Specifically, materials with low loss tangents will provide a sensor with higher Q factors.

The body of the implantable sensor of the disclosed embodiment of the present invention is preferably constructed of ceramics such as, but not limited to, fused silica, quartz, pyrex and sintered zirconia, that provide the required biocompatibility, hermeticity and processing capabilities. These materials are considered dielectrics, that is, they are poor conductors of electricity but are efficient supporters of electrostatic or electroquasistatic fields. An important property of dielectric materials is their ability to support such fields while dissipating minimal energy. The lower the dielectric loss, the lower the proportion of energy lost, and the more effective the dielectric material is in maintaining high Q.

With regard to operation within the human body, there is a second important issue related to Q, namely that blood and body fluids are conductive mediums and are thus particularly lossy. As a consequence, when a sensor is immersed in a conductive fluid, energy from the sensor will dissipate, substantially lowering the Q and reducing the sensor-to-electronics distance. It has been found that such loss can be minimized by further separation of the sensor from the conductive liquid. This can be accomplished, for example, by coating the sensor in a suitable low-loss-tangent dielectric material. The potential coating material must also meet stringent biocompatibility requirements and be sufficiently compliant to allow transmission of fluid pressure to the pressure-sensitive deflective region. One preferred material for this application is silicone rubber. It should be appreciated that use of a coating is an optional feature and is not required to practice the invention per se but such coatings will preserve the Q of the sensor which can prove advantageous depending on the intracorporeal location of the sensor.

There are various manufacturing techniques that can be employed to realize sensors according to the current invention. Capacitors and inductors made by a variety of methods can be manufactured separately, joined through interconnect methods and encapsulated in hermetic packaging. In one embodiment, the pressure sensitive capacitor 15 and the three-dimensional inductor coil 20 are formed separately and joined together to form the LC circuit. In another embodiment, the capacitor and inductor coil can be manufactured integral with one another. Additionally, there are several methods to create these discrete elements and to join each discrete element to create the final sensor. The following examples are provided to illustrate important design considerations and alternative methods for creating these discrete sensor elements but should not be construed as limiting the invention in any way.

Figure 12:
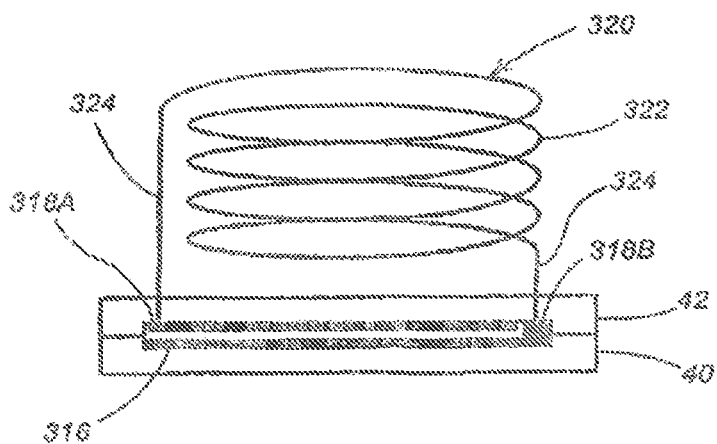
FIG. 12 is a schematic view of still another embodiment of an implantable, wireless pressure sensor.

Referring to FIG. 12, the inductor coil 320 is comprised of the inductor coil body 322 and the coli leads 324. Numerous parameters of the inductor coil can be varied to optimize the balance of size and electrical properties of the circuit, including the materials, coil diameter, wire gage, insulation thickness, number of coil windings, and cross-sectional area of the coil body. The material comprising the coil must be highly conductive and also biocompatible. Suitable materials include, but are not limited to, gold, copper, and alloys thereof.

It is preferable in the practice of the disclosed invention to minimize or eliminate changes in resonant frequency of sensors of the invention due to factors other than capacitance in order to reliably correlate the shift in resonant frequency with a change in distance between the capacitor plates. Thus, it is important that the inductor coil 320 in sensors of the current invention maintain a high degree of mechanical stability as a change in coil position relative to the capacitor or a change in coil configuration will cause the resonant frequency of the device to change. There are many ways to immobilize the inductor coil 320 of the present invention. If the wire used to construct the coil is sufficiently strong, the coil can be self-supporting, also known as an "air core" configuration. A solenoid coil is another suitable configuration. If the wire is not sufficiently strong to maintain its intended configuration during assembly and in use, the coil can be formed around a central bobbin comprised of a suitable material. Such bobbins can be configured to be mechanically fixed to any surface or combination of surfaces defining the coil receiving trench via a press fit. Alternatively, the coil can be wound on a thermoplastic bobbin where the thermoplastic material can be subjected to sufficient heat to cause flow to encapsulate and/or adhere to the surface of the coil receiving trench.

Alternatively, a thermosetting or thermoplastic polymer with good high temperature characteristics, low loss tangent, and, optionally, low dielectric constant material can be used to support the coil. The polymer should also be highly inert, have excellent aging resistance and exhibit substantially no moisture absorbance or outgassing. With the use of a thermosetting material, the polymer is applied to the coil in liquid form and allowed to cure or otherwise harden. Thermoplastic materials can be preformed and inserted between the coil and at least one coil receiving trench wall and subsequently heated to achieve sufficient flow to encapsulate and/or adhere to the coil and at least one coil receiving trench wall.

Polyimide, fluorinated polymers, glass frit, ceramic paste and liquid crystal polymer are examples of suitable materials for immobilizing the inductor coil 320 due to their thermal, electrical, and mechanical properties. However, manufacturing processes achieving substantially similar results that involve lower processing temperatures would make other material choices desirable, such choices being obvious to one skilled in the art.

The wire from which the coil is formed can be solid wire, bundled wire or cable, or individually insulated stranded wire.

The wire gage, coil diameter, cross-sectional area of the coil body, and number of windings all influence the value of inductance and the detection range of the circuit. As any of these properties increase, so do the size and the inductance of the coil, as well as the sensor-to-electronics distance. To specify an inductor coil for use in the sensor, size considerations must be balanced with those of inductance and Q.

A small scale three-dimensional inductor coil can be formed in a variety of ways. It can be created conventionally. One such method is machine coil winding of small diameter insulated magnet wire, as shown in FIG. 1.

Figure 13:
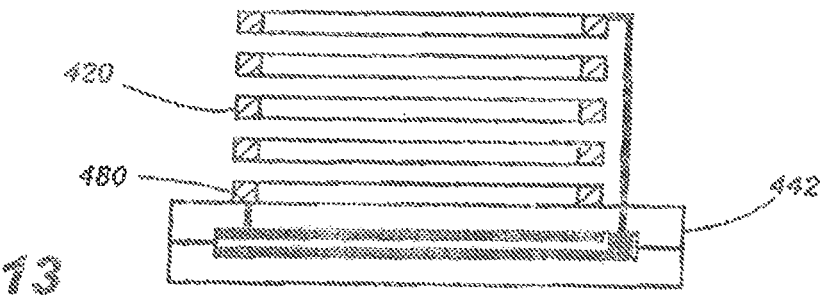
FIG. 13 is a schematic view of a further embodiment of an implantable, wireless pressure sensor in which a three-dimensional inductor coil is built onto the top of through connection terminals on the backside of a capacitor plate substrate.

In another embodiment, shown in FIG. 13, a three-dimensional inductor coil 420 is built onto the top of one of the through connections terminals 480 on the backside of the capacitor plate substrate 442, using integrated circuit processing techniques and a multitude of layers. This coil 420 can be defined and supported by photo-definable dielectric material such as photo-definable polyimide. In the disclosed embodiment, the coil is free standing in air, supported by same-material mechanical elements that are strategically positioned to minimize the effect of the supporting mechanical elements on the electrical function of the coil.

Figure 14:
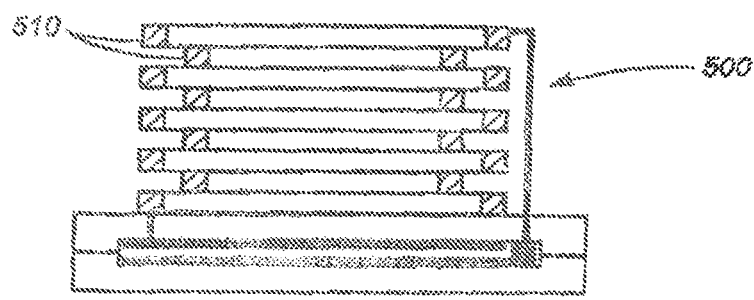
FIG. 14 is a schematic view of another embodiment of a wireless pressure sensor in which each subsequent layer is alternately spaced slightly smaller or larger in diameter than the previous winding.

In this approach it is desirable to minimize the number of design layers to improve batch process yield and to reduce processing time. In a conventional configuration, such as that shown in FIG. 13, a spacing layer is required between each winding, making the number of layers required equal to two times the number of windings. In one version 500 of the three-dimensional coil design, an example of which is shown in FIG. 14, each subsequent coil 510 is alternately spaced slightly smaller or larger in diameter than the previous winding. This configuration creates a small separation between adjacent coils 510 in the x-y plane, eliminating the need for an extra vertical spacing layer in between windings. This configuration results in a number of coil windings equal to the number of layers, which is more practical for manufacturing using a MEMS approach.

Figure 15:
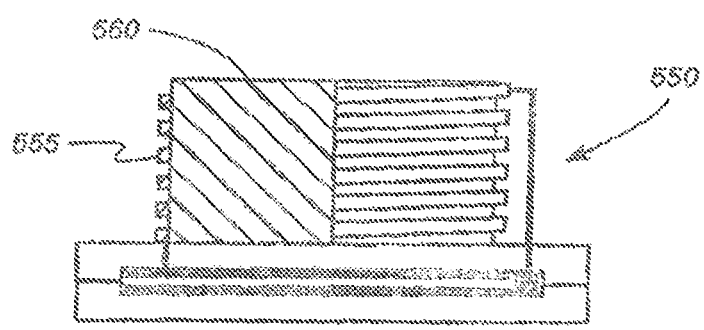
FIG. 15 is a schematic view of a further embodiment of an implantable, wireless pressure sensor in which a three-dimensional inductor coil is built onto the surface of a cylinder.

In yet another embodiment 550, shown in FIG. 15, a three-dimensional inductor coil 555 is built onto the surface of a cylinder 560 of an appropriate material such as, but not limited to fused silica. A conductive layer is first applied to the surface of the cylinder 560. Then a mold is formed onto the surface so that parts of the underlying conductive surface are exposed and some are covered. A metal may then be formed onto the exposed areas by electroplating, sputtering or vapor deposition. The exposed area forms a helical trench that extends along the surface of the cylinder, thus realizing an inductor coil.

Figure 2:
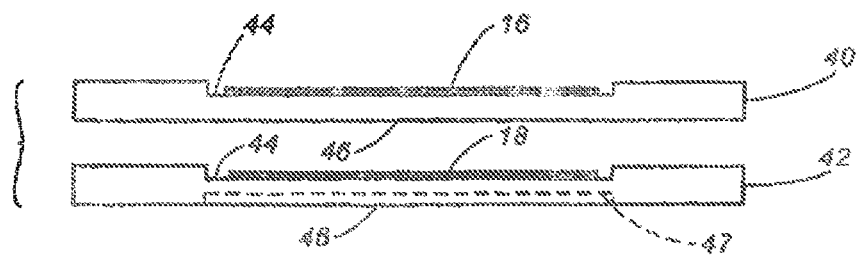
FIG. 2 is a schematic view of two pressure sensitive capacitor plates being formed in recessed trenches on two substrate wafers.

Referring now to FIG. 2, the pressure sensitive capacitor plates 16, 18 are formed on two separate substrate wafers 40, 42 in recessed trenches 44. At least one of the wafers 40 has a substrate thickness in the region 46 of the capacitive plate 16 such that sufficient pate deflection occurs due to external pressure change, resulting in a sufficient change in resonant frequency per unit pressure (mm Hg) once the LC circuit has been created. If necessary, the thickness of the wafer 40 in the region 46 can be reduced by suitable chemical or mechanical means, as indicated by the dashed line 47, to provide the desired range of deflection.

Figure 3:
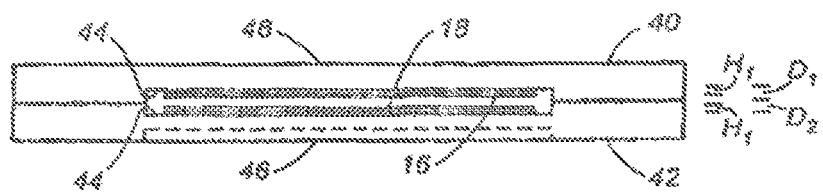
FIG. 3 is a schematic view showing the wafers of FIG. 2 imposed in face-to-face relation.

As shown in FIG. 3, the wafers 40, 42 are bonded together such that the capacitive plates are 16, 18 parallel and separated by a gap on the order of 0.1-10 microns, preferably 0.1-2 microns.

The performances of the sensor, especially the propensity of its capacitance and, in turn, its resonant frequency to change as a response to an environmental pressure change, are closely related to few fundamental geometrical considerations. Widening or elongating the deflective region will augment its mechanical flexibility, and, in turn, the pressure sensitivity of the sensor. Decreasing the thickness of the deflective area will result in similar improvements. However, thinner deflective region can become too fragile or otherwise more sensitive to systemic response from the host-organism other than changes in mean and pulsatile blood pressure (ex: hyperplasia, tissue overgrowth, etc.). Reducing the gap, while maintaining adequate deflective region thickness, offers a complementary alternative to insufficiently low sensitivity. As the initial value of the gap is shrinking, the motion of the deflective region relative to the initial gap becomes proportionally more important. This results in a greater change in capacitance for a given stimulus, therefore enhancing the pressure sensitivity. While relevant sensitivity can be achieved with initial air-gap ranging from 0.1 to 10 micrometers, initial air-gaps ranging from a 0.1 to 2 micrometers are preferable.

To ensure adequate pressure range, the value of the maximum deflection under maximum load (indexed, for exampled, on physiologically relevant maximum pulsatile blood pressure values, at relevant location in the host-organism) ought to be, in theory, inferior or equal to the value of the initial gap. In practice, limiting the maximum deflection under maximum bad to represent only a fraction of the initial gap (ex: 0.6 micrometer for a 1 micrometer initial gap) will ease the fabrication constraints and result in a more robust and versatile sensor.

One suitable method for creating the pressure sensitive capacitor is by electroplating the individual plates 16, 18 in the recessed trenches 44 on a substrate wafer 40, 42 to a given height H1, H2 that is less than or equal to the depth D1, D2 of the respective trench 44. When the wafers are bonded together the capacitive plates are generally separated by the difference between the sum of the trench depths and the sum of the plate heights, (D1+D2)−(HI+H2). An inherent variation in the height of the plates and the required range of deflection for the full operating pressure range are parameters, which determine the initial separation distance (a.k.a. the gap).

Figure 4:
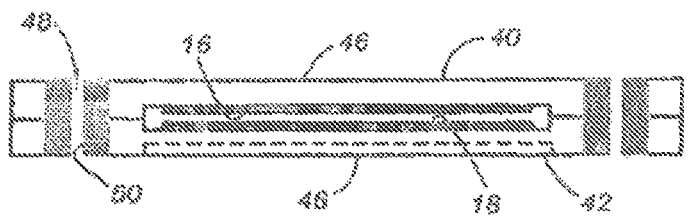
FIG. 4 is a schematic view showing the imposed wafers of FIG. 3 being laser-cut around their peripheries.

FIG. 4 illustrates the assembled wafers and capacitor plates laser-cut around their peripheries 48, reducing the capacitor to its final size and hermetically fusing the two wafers together at 50. A $CO_2$ laser can be used at a peak wavelength of about 10 microns if the substrate is fused silica. Power must be sufficiently large to cut and fuse the wafers together, while at the same time being sufficiently small that the internal components of the sensor are not damaged by excessive heat.

In an alternate method, the wafers are pre-bonded using glass frit to produce a hermetic seal around the cavities. In this method, the laser cut only releases the sensors from the wafer, and does not provide the primary means of creating the hermetic seal. Other suitable methods of hermetically sealing the wafers include, but are not limited to, adhesives, gold compression bonding, direct laser bonding, and anodic bonding.

Figure 5:
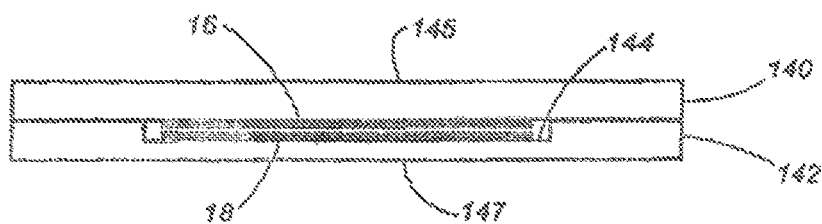
FIG. 5 is a schematic view of an alternate embodiment of two imposed wafers in which only one of the wafers has a recessed trench.

In an alternate embodiment illustrated in FIG. 5, one plate 18 is formed on a substrate wafer 142 having a trench 144 with a depth greater that of the trench 44 in the substrate wafer 40. The other plate 16 is formed on the inner surface of a wafer 140 without a trench. When imposed in face-to-face relation, the plate 16 is received into the lower end of the trench 144 with the plates 16, 18 disposed in parallel, spaced-apart relation.

Figure 6:
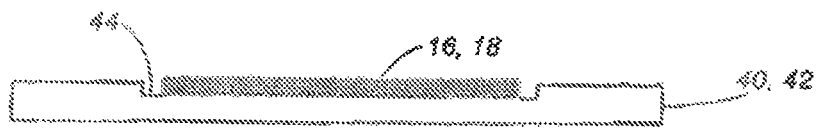
FIG. 6 is a schematic view illustrating a first step in a process for manufacturing wafers with capacitor plates formed thereon.

To achieve smaller gap separation distances on the order of 0.1-2 microns, revised processing methods are employed to bring additional control to the variation in height across the conductive plates 16, 18. One method is as follows: the conductive plate 16, 18 is built to a target height that slightly exceeds the depth of the recess trench 44, as shown in FIG. 6. In the disclosed embodiment the plates are formed by electroplating. Preferred materials for the plates are copper, gold, and alloys thereof. After building the plates, each conductive plate 16, 18 is polished using chemical/mechanical polishing (CMP) to planarize and reduce the height of the plate until it is less than the depth of the trench by the desired amount, as shown in FIG. 9.

Figure 7:
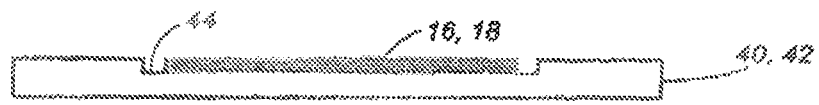
FIG. 7 is a schematic view illustrating a second step in a process for manufacturing wafers with capacitor plates formed thereon.

Another method also begins with the plates 16, 18 formed to a height that slightly exceeds the depth of the trenches 44, as shown in FIG. 6. The metal capacitor plates 16, 18 are mechanically polished to planarize the metal surface down to the surface of the substrate 40, 42, as shown in FIG. 7.

Figure 8:
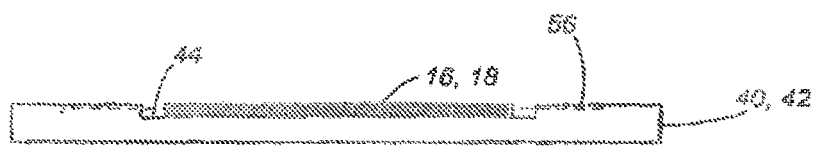
FIG. 8 is schematic view illustrating a third step in a process or manufacturing wafers with capacitor plates formed thereon.
Figure 9:
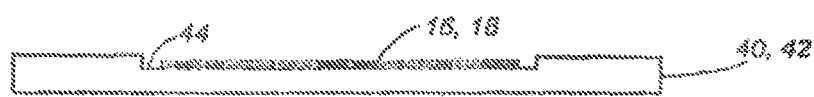
FIG. 9 is a schematic view illustrating a fourth step in a process for manufacturing wafers with capacitor plates formed thereon.

Following this step, the metal plates are chemically etched by a selective etchant to the height indicated by the dashed line 56 in FIG. 8 to achieve the desired difference in height between the height of the plate 16, 18 and the depth of the trench 44, as shown in FIG. 9.

Still another method for forming the plates is physical vapor deposition (PVD), also known as thin film deposition, in conjunction with photolithography. PVD is used to deposit a uniform layer of metal, sub-micrometer to tens of micrometers thick, on a wafer. Subsequently a layer of photoresist is deposited, a mask is used to pattern the photoresist, and a selective etching technique is utilized to etch away the extra metal and to define the desired pattern. Other methods of defining the metal pattern can be utilized, such as, shadow masking, a method well known in the art.

Figure 10:
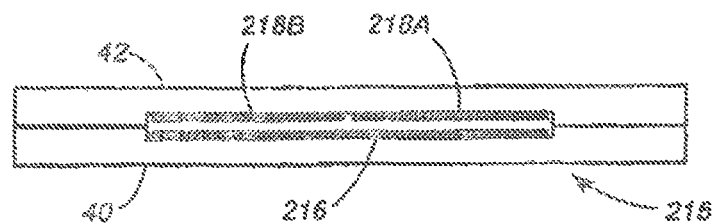
FIG. 10 shows another embodiment in which two capacitor plates are formed on one wafer.
Figure 11:
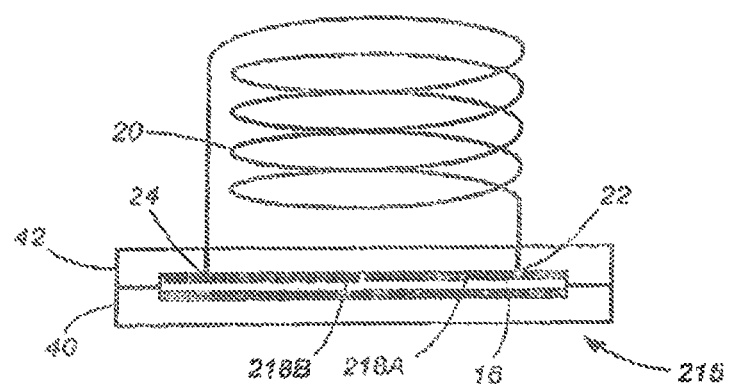
FIG. 11 illustrates the embodiment of FIG. 10 showing the two capacitor plates on the single wafer connected to opposite ends of a helical inductor coil.

In one approach, shown in FIGS. 10 and 11, a pressure sensitive capacitor 215 can be formed by separating the bottom conductive pad into two separate regions 218A, 218B that capacitively couple to one another via a common third conductive region 216 on the pressure sensitive deflective region. The inductor coil 20 is then electrically connected as shown in FIG. 11, one lead 22 of the coil 20 to the first region 218A, and the other lead 24 of the coil 20 to the second region 218B.

When the split-plate design is employed for one side of the capacitor, as shown in FIG. 11, the spat plates 218A, 218B are preferably located on the fixed side of the capacitor (i.e., opposite the pressure-sensitive side), because the electrical/mechanical interconnects made to the spot plates in order to complete the LC circuit are less prone to mechanical failure when the surface to which they are mechanically attached does not deflect or move repetitively.

In yet another embodiment, shown in FIG. 12, the plate on the top wafer 42 is separated by a dielectric into two conductive regions 318A, 318B, with one region 318B substantially larger than the other 318A. After bonding together of the two wafers 40, 42, the smaller conductive region 318A is electrically connected to the outer edge of the pressure sensitive plate 316, spanning the air gap with a laser weld that is performed through the substrate material. The laser wavelength is selected so that it is passes through the substrate material with minimal energy absorption, but heats the conductive plate sufficiently to produce the weld connection between the top and bottom plates 316, 318A.

It will be appreciated that sensors embodied by the current invention can have capacitive and inductive elements maintained in separate hermetic cavities or that these elements may be contained in a single hermetic cavity.

Figure 22:
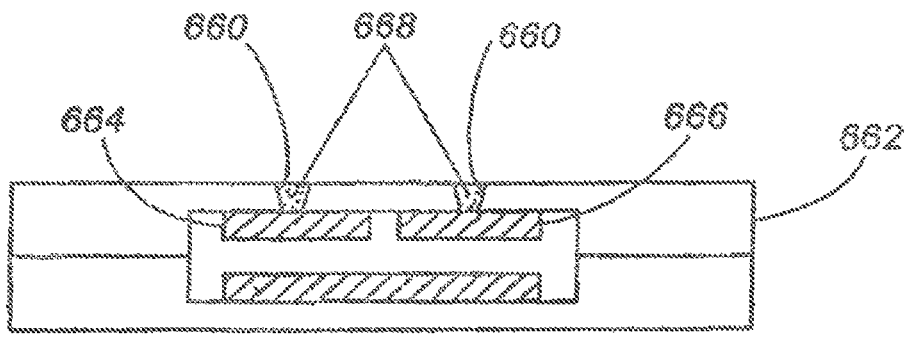
FIG. 22 shows a first arrangement for electrically and mechanically interconnecting a capacitor plate to an inductor coil.

In one embodiment, the pressure sensitive capacitor 15 needs to be connected to the three-dimensional inductor coil 20 while maintaining a hermetic seal around the internal cavity that defines the separation gap between the capacitive plates 16, 18. This can be achieved by using a variety of through-wafer interconnection methods, familiar to those skilled in the art. Referring to FIG. 22, through holes or vias 660 are formed in an upper wafer 662 to provide mechanical and electrical access to a pair of upper capacitor plates 664, 666. The wafer through-holes can be formed before or after plate formation using some combination of the following techniques: laser drilling, chemical (wet) etching, conventional or ultrasonic machining, or dry etching. As shown in FIG. 22, the vies 660 can optionally be filled with gold, copper, or other suitable conductive material to form through-wafer interconnects 668 in conductive communication with the capacitor plates 664, 666. The through-wafer interconnects 668 thus form a hermetic seal. Leads from an inductor coil (not shown) are attached to the through-wafer interconnects 668 to place the leads m conductive communication with the capacitor plates 664, 666.

Figure 23:
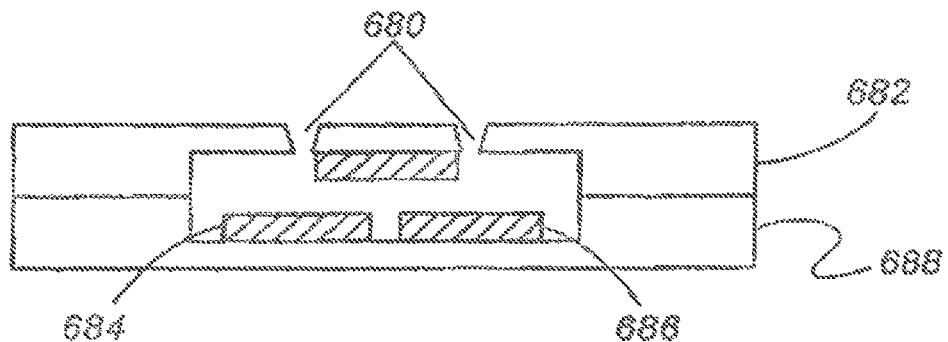
FIG. 23 shows a second arrangement for electrically and mechanically interconnecting a capacitor plate to an inductor coil.

Referring to FIG. 23, through holes or vies 680 are formed in an upper wafer 682 to provide mechanical and electrical access to a pair of lower capacitor plates 684, 686. Electrical connections to the lower capacitor plates 684, 686 will be accomplished through leads of the inductor coil (not shown) or through wires or other suitable conductive means.

Thermosonic or ultrasonic bonding can be used to connect the inductor coil to either an electrode of a capacitor or a through-wafer interconnect. Thermosonic and ultrasonic bonding are types of wire bonding used for metal wires including, but not limited to, gold wires. Typical temperatures required for thermosonic bonding are between 125-220° C., and bonding occurs when a combination of static and ultrasonic mechanical and thermal energy is delivered to the metallic coil wire to be bonded to a metal surface. Ultrasonic bonding is performed just as thermosonic bonding but without the use of heat. Useful materials for the metallized bond sites and coil comprise gold, copper and aluminum and alloys thereof. Bonds can be formed between certain dissimilar metals as well as between all like metals, and such combinations are widely known in the art.

If the metal or metal alloy used for the coil has a dielectric (e.g., polymer) coating, the coating must be removed prior to bonding. The coating can be removed to expose the metal at the adhesion point so that bonding can occur by either mechanical or chemical means. Alternatively, the parameters (e.g. time, heat, pressure) of the thermosonic bonding process can be altered and the geometry of the bonding tool modified so that reliable mechanical and electrical interconnects are created. Such modifications cause the coating material to be pushed aside, exposing the metal at the bonding site and extruding the wire slightly. This latter technique provides certain advantages because it reduces the number of manufacturing steps.

An alternate method of conductively connecting the coil to the capacitive plates is the solder bump. Solder is applied to the metal-metal interface of the coil and electrode or interconnect to form a mechanical and electrical connection. This method can be used for capacitor plate or through-wafer interconnections. Lead-free solder should be used for biocompatibility. Connection can also be achieved through IC processing techniques, which allow for plates and coils to be formed in electrical contact with one another. Finally laser welds, as previously discussed, can be used to achieve electrical/mechanical interconnects.

Figure 16:
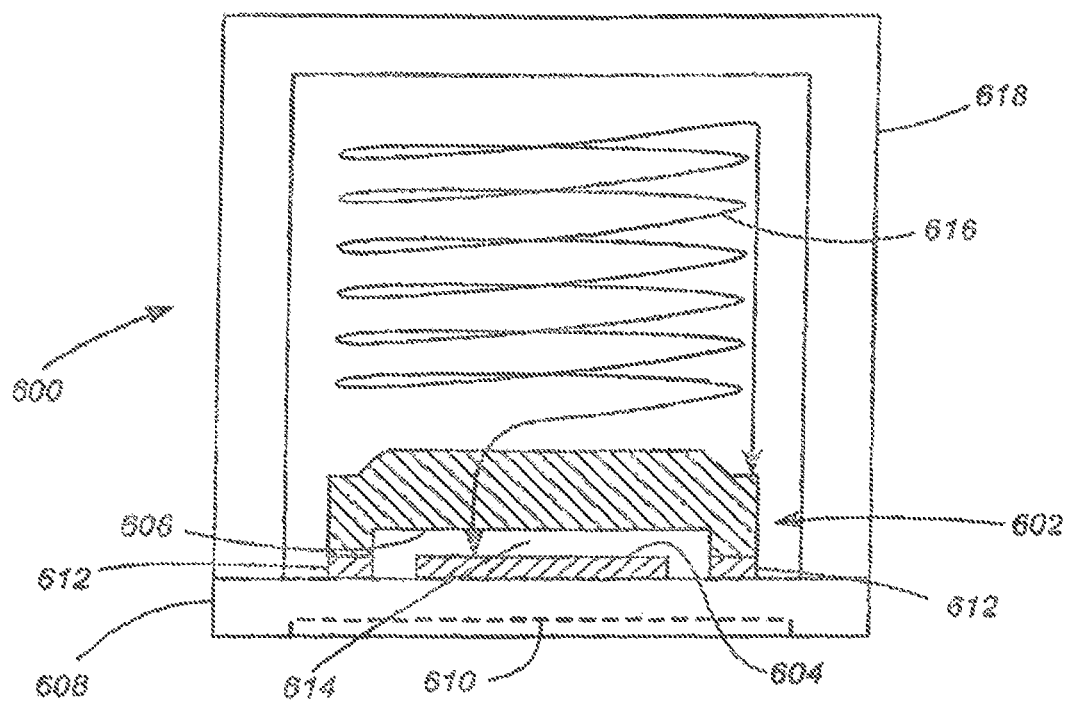
FIG. 16 is a schematic view of another embodiment of a wireless pressure sensor in which the pressure sensitive capacitor and three-dimensional inductor coil are formed together on one wafer.

FIG. 16 illustrates a surface micromachined, capacitor coupled sensor 600. The capacitor structure 602 comprises at least two plates 604, 606, at least one 604 of which is built directly atop a first wafer 608. This plate 604 will be referred to as the bottom plate. The region of the wafer 608 where the bottom plate 604 is built will be referred to as the deflective region 610. If necessary, the thickness of the wafer 608 in the region of the deflective region 610 can be reduced in thickness to enhance its deformability.

The other plate 606 is suspended above the bottom plate 604. The top plate 606 is mechanically anchored to the deflective region by pillar-like supporting elements 612 located at the periphery of the bottom plate 604. Bottom and top plates 604, 606 are electrically insulated and physically separated from one another by an air gap 614. The top electrode 606 mechanical design, material and dimensions are carefully chosen so that the suspended part of the electrode does not structurally deform under its own weight or creep over time.

A coil 616 of relevant geometry and inductance value is built or assembled using, as an example, any of the methods described herein. Its terminals are electrically and mechanically connected to either one of the opposite plates 604, 606 of the capacitor 602. A capsule 618 or other form of hermetic surrounding is used to encapsulate both the coil 616 and capacitor 602.

To achieve the desired pair of fixed and suspended plates 604, 606, the fabrication process of the disclosed embodiment employs a technique known in the art as "sacrificial layer." A sacrificial layer is a structural layer that remains buried throughout the fabrication process under various layers of material until it can be removed, releasing the structures and layers built on top of the sacrificial layer. Once removed, a void remains in place of the sacrificial layer. This void forms the air gap that separates top from bottom plate(s).

A sacrificial layer must abide by at least two rules: (1) it must remain unaffected (no cracking, peeling, wrinkling, etc.) during the entire fabrication process until it is removed, and (2) selective and efficient removal techniques must exist to remove it without adverse consequences to any remaining structures.

Figure 17:
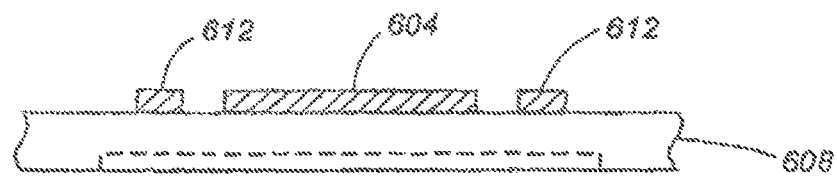
FIG. 17 is a schematic view showing a first step in the manufacturing process of the wireless pressure sensor of FIG. 16.

Referring now to FIG. 17, the fabrication of the capacitor 602 starts with the creation of the bottom plate 604 on the wafer 808, using physical vapor deposition and photolithography. The backside of the wafer 608 is optionally thinned to enhance compliance in the deflective region 610 of the wafer at the location of the bottom plate 604 so as to facilitate deflection when a force or a pressure is applied.

The anchoring sites 612 are defined at the periphery of the bottom plate 604. Anchoring sites 612 are small enough to represent only a fraction of the footprint of either bottom or top plate 604, 606. However, they are big enough to insure reliable mechanical anchoring for the top plate 606.

Figure 18:
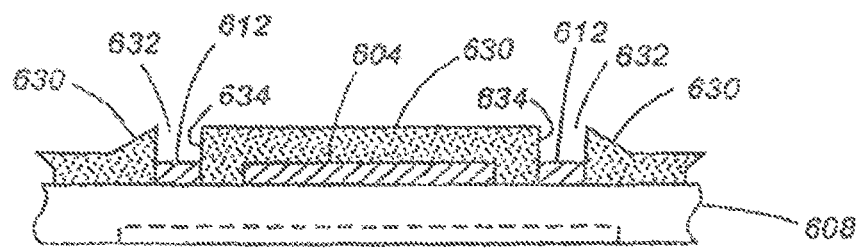
FIG. 18 is a schematic view showing a second step in the manufacturing process of the wireless pressure sensor of FIG. 16.

Referring now to FIG. 18, a layer 630 of material with desirable physical and chemical traits is deposited onto the wafer 608 over the bottom plate 604 and the anchoring sites 612 to serve as a sacrificial layer. The sacrificial material is, but is not limited to, a thin film of photo-definable polymer (the first polymer layer). The thickness of the polymer is tuned by altering the conditions during deposition. Film thicknesses ranging from fractions of micrometers to tens of micrometers are achieved routinely. To insure that the layer 630 of photo-definable polymer remains unaffected (no cracking, peeling, wrinkling, etc.) during the entire fabrication process until it is removed, proper curing and cross-linking precautionary steps must be taken.

With further reference to FIG. 18, using photolithography, windows 632 are opened in the first polymer layer 630. The window geometry and in-plane location corresponds to those of the anchoring sites 612. Because the photo-definable polymer has a non-null thickness, each opening (a.k.a. window) in the first polymer layer is surrounded by sidewalls 634 which height corresponds to the thickness of the first polymer layer.

Figure 19:
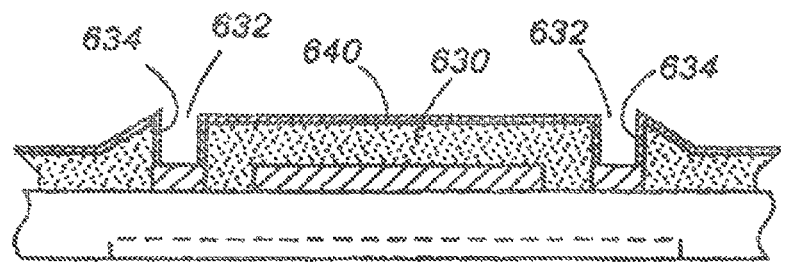
FIG. 19 is a schematic view showing a third step in the in a manufacturing process of the wireless pressure sensor of FIG. 16.

A thin film metallic layer 640 is then deposited on top of the sacrificial layer 630, as depicted in FIG. 19. This layer comprises a seed layer, as it will provide a site upon which electroplated metals can grow later on. The method of deposition should insure that the metallic film 640 evenly coats the upper surface of the sacrificial layer 630 (the first polymer layer) as well as the sidewall 634 and the bottom areas of the windows 632 previously defined in the sacrificial layer.

Figure 20:
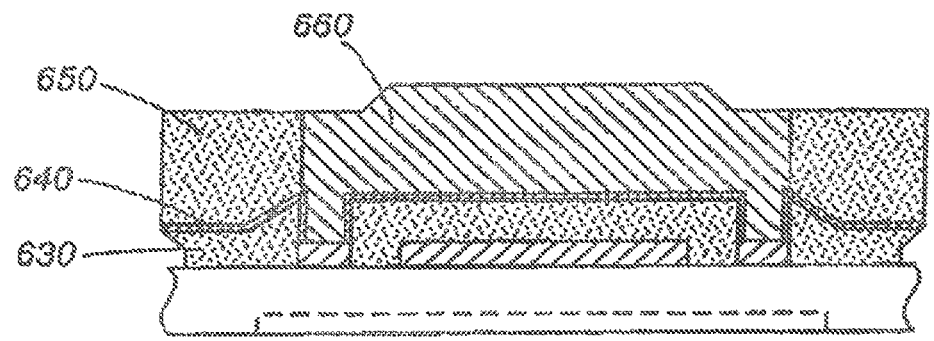
FIG. 20 is a schematic view showing a fourth step in the manufacturing process of the wireless pressure sensor of FIG. 16.

Referring now to FIG. 20, a second layer 650 of photo definable polymer (the second polymer layer) is deposited and patterned using photolithography. During this process, selected regions are removed from the surface of the substrate, defining new windows 652 (large openings) in the second polymer layer 650 without affecting any other previously deposited layer (especially the first polymer layer 630). The in-plane geometry of the new windows represents the in-plane geometry of the top electrode 606 (FIG. 17). The geometry of the new windows extends to encompass the geometry and location of the anchor sites 612.

Regions where the photo definable polymer has been removed are subjected to a method known as electroplating. In that fashion, metals like copper or gold can grow and adhere in the presence of the seed layer. The electroplating occurs at the same time at the anchoring sites, on the sidewalls, and on any other region exposed through windows opened in the second polymer layer. The resulting structure is a continuous electroplated film 660 of the desired thickness. The thickness can range from few micrometers to few tens of micrometers. Electroplated copper is preferred for its ease of deposition and low cost.

Figure 21:
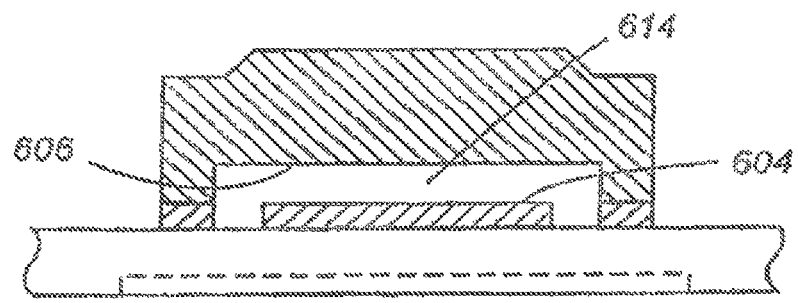
FIG. 21 is a schematic view showing a fifth step in the manufacturing process of the wireless pressure sensor of FIG. 16.

Next, as shown in FIG. 21 the second polymer layer 650, the metal layer 640, and the sacrificial layer 630 are removed using wet or dry selective removal techniques. The preferred removal technique for both the second polymer layer 650 and the sacrificial layer 630 is wet dissolution in appropriate solvents such as acetone. At this point, both bottom and top plates 604, 606 are formed. The top plate 606 is suspended above the bottom plate 604 and separated from it by an air gap 614, which corresponds to the thickness of the first polymer layer.

As the fabrication of the sensor continues, the coil 616 is bunt or assembled using any of the methods described herein. Its terminals are electrically and mechanically connected to either one of the opposite plates 604, 606 of the capacitor 602. Finally, as shown in FIG. 16, the capsule 618 or other form of hermetic surrounding is assembled onto the wafer 608 to encapsulate the coil 616 and capacitor 602.

A variation on the two-wafer design is shown in FIGS. 24-28. A sensor 700 comprises a thick upper wafer 702 and a thinner lower wafer 704. The thin lower wafer 704 comprises the pressure-sensitive deflective region portion 706 of the sensor 700. A notch 708 is optionally formed in the upper wafer 702 to accommodate an anchor, such as a corkscrew, hook, barb, or other suitable stabilization means. The notch can be created on the backside of the wafer directly if the cap is sufficiently thick to accommodate the notch and a separation distance between the bottom of the notch and the coil body without causing any parasitic, deleterious electromagnetic or mechanical effects on the sensor function. Alternatively, the notch can be created by using wet or dry methods in a separate wafer or plurality of wafers and then bonded to the backside of the sensor. The notch can have a variety of regular or irregular geometries and can have rough or smooth sidewalls—any configuration achievable by conventional technologies that would impart some advantage or feature to assist in fixing the anchor mechanism to the sensor.

A capacitor 710 comprises a power plate 711 formed on the inner surface of the lower wafer 704 and an opposing pair of upper plates 712, 714 formed on the lower surface of the upper wafer 702. A channel 716 is formed in the upper wafer 702 to receive an inductor coil 718. The inductor coil 718 includes leads 720 that conductively connect the opposite ends of the coil to the upper plates 712, 714.

Figure 25:
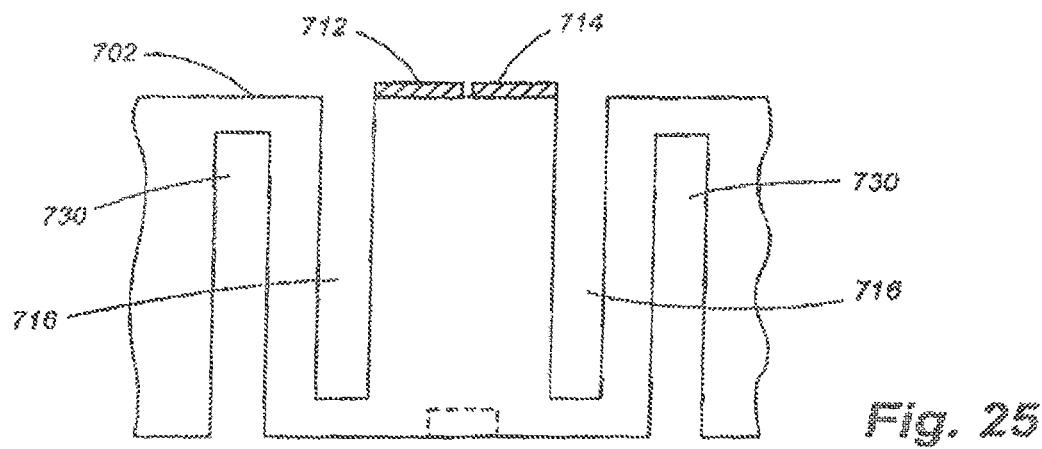
FIG. 25 is a schematic view showing a first step in the manufacturing process of the wireless pressure sensor of FIG. 24.

Manufacture of the sensor 700 will be explained with reference to FIGS. 25-28. Referring first to FIG. 25, a dicing trench 730 is formed in the lower portion of the upper wafer

702 (shown inverted for the manufacturing process). The dicing trench 730 is a feature, which comprises a reduction in thickness of the wafer 702 along a line that defines the perimeter of the sensor 700. The dicing trench 730 is advantageous where reduction of the amount of energy transferred to the sensor during dicing is needed, for example, to protect the sensor from heat damage when dicing with a laser. When the wafer thickness is reduced, less energy is required to cut the sensor from the rest of the wafer, and thus less thermal energy is transferred to the critical components of the sensor.

As can also be seen in FIG. 25, the channel 716 is formed in the upper surface of the upper wafer 702. The lower capacitor plates 712, 714 are formed on the upper surface of the upper wafer 702.

Figure 24:
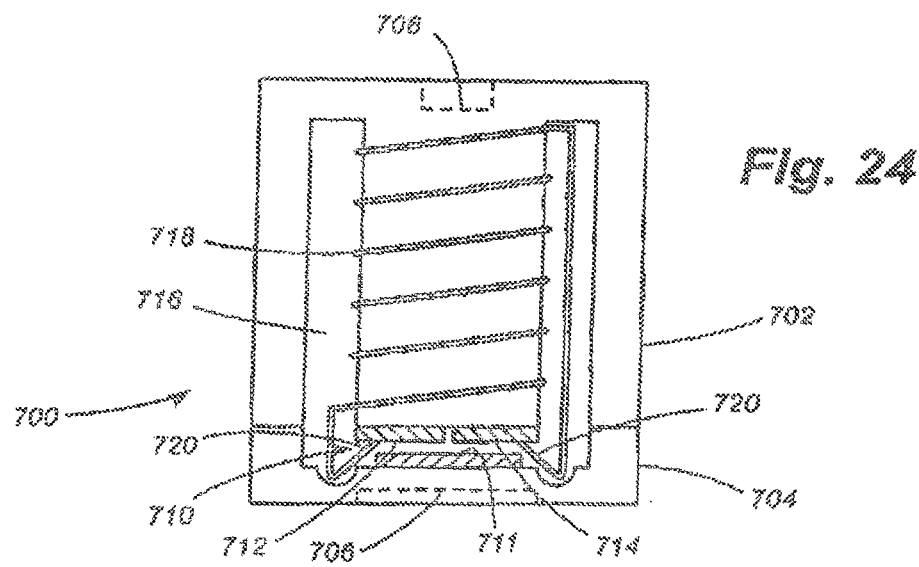
FIG. 24 is a schematic view of another embodiment of a wireless pressure sensor in which the pressure sensitive capacitor and three-dimensional inductor coil are formed on two wafers.
Figure 26:
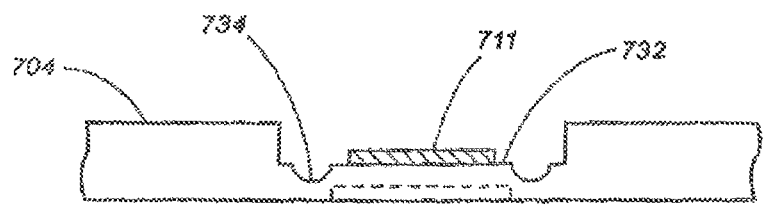
FIG. 26 is a schematic view showing a second step in the manufacturing process of the wireless pressure sensor of FIG. 24.

Referring now to FIG. 26, a recess 732 is formed in the upper surface of the lower wafer 704. The recess optionally includes troughs 734 for providing clearance for the leads 720 of the inductor coil 718 (FIG. 24). The lower capacitor plate 711 is formed in the base of the recess 732 in the upper surface of the lower wafer 704.

Figure 27:
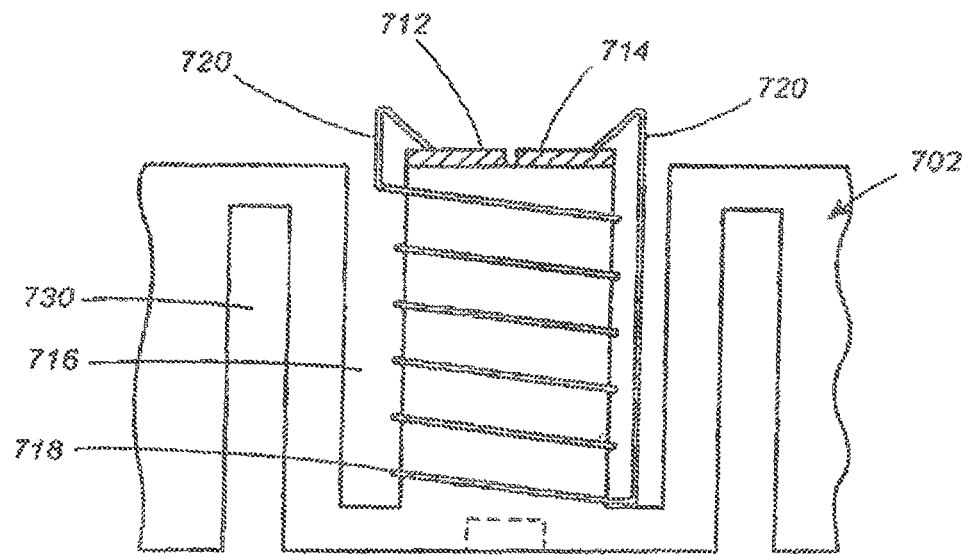
FIG. 27 is a schematic view showing a third step in the manufacturing process of the wireless pressure sensor of FIG. 24.

Referring now to FIG. 27, the inductor coil 718 is introduced into the annular recess 716 of the upper wafer 702. The two leads 720 of the inductor coil 718 are connected to the upper capacitor plates 712, 714.

Figure 28:
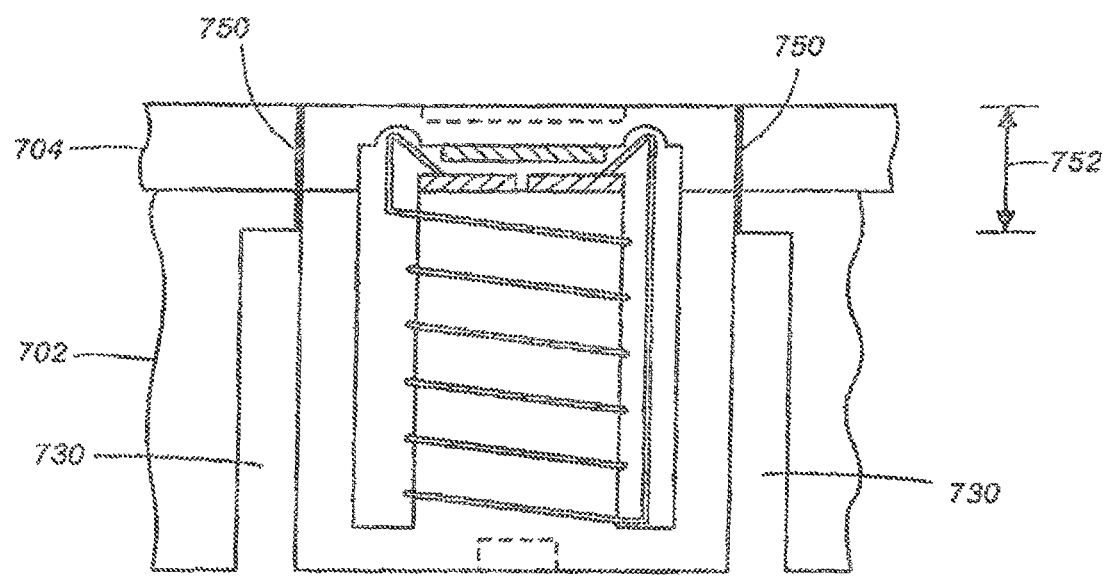
FIG. 28 is a schematic view showing a fourth step in the manufacturing process of the wireless pressure sensor of FIG. 24.
Figure 29:
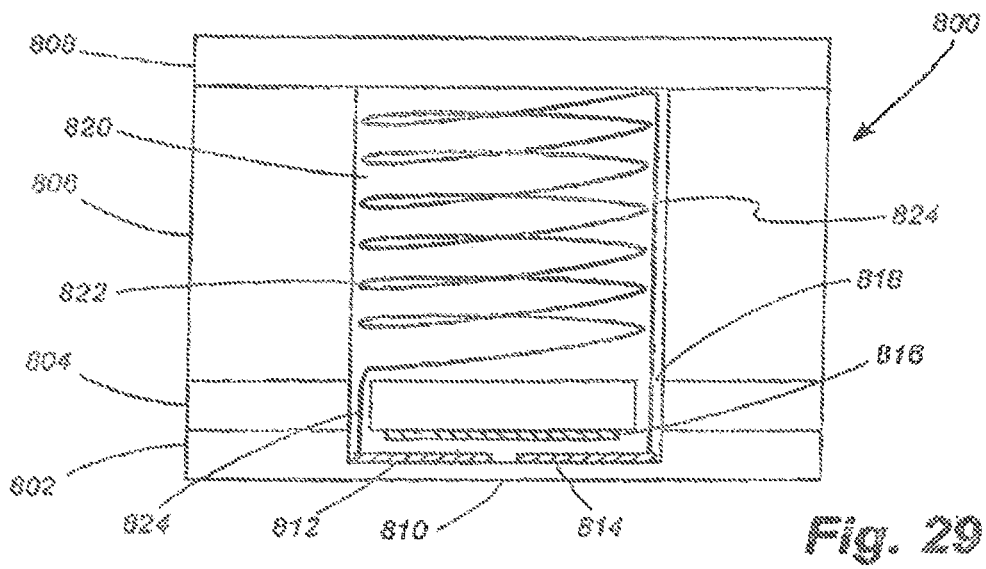
FIG. 29 is a schematic view of an embodiment of a wireless pressure sensor utilizing four wafers.

Referring to FIG. 28, the lower wafer 704 is now inverted and positioned atop the upper wafer 702. A laser is then used to cut and simultaneously heat bond the wafers 702, 704 at the lines 750 to complete fabrication of the sensor 700. Because of the presence of the dicing trenches 730, the laser need cut through only a thickness corresponding to the double arrow 752. This shallow cut minimizes the amount of thermal energy transferred to the internal components of the sensor.

FIGS. 29-32 depict an embodiment of a sensor 800 manufactured from four stacked wafers, 802, 804, 806, and 808. The bottom wafer 802 comprises the pressure-sensitive deflective region 810 and a pair of capacitor plates 812, 814 formed on its upper surface. The second wafer 804 comprises a capacitor plate 816 formed on its lower surface and a pair of through-holes 818 for electrical connections. The third wafer 806 comprises a cylindrical cavity 820 for accommodating an inductance coil 822. Leads 824 of the inductance coil 822 extend through the holes 818 in the second wafer 804 and connect to the capacitor plates 812, 814. The fourth wafer 808 fits atop the third wafer to provide a sealed structure.

Figure 30:
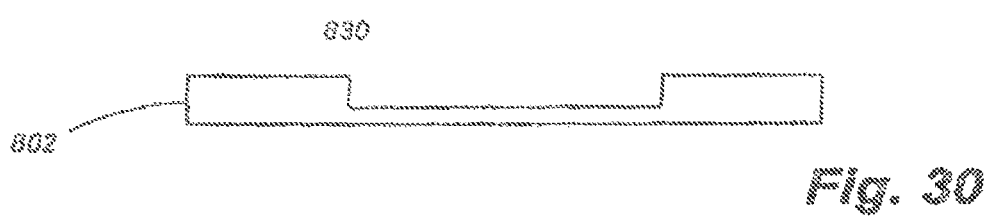
FIG. 30 is a schematic view showing a first step in the manufacturing process of the wireless pressure sensor of FIG. 29.
Figure 31:
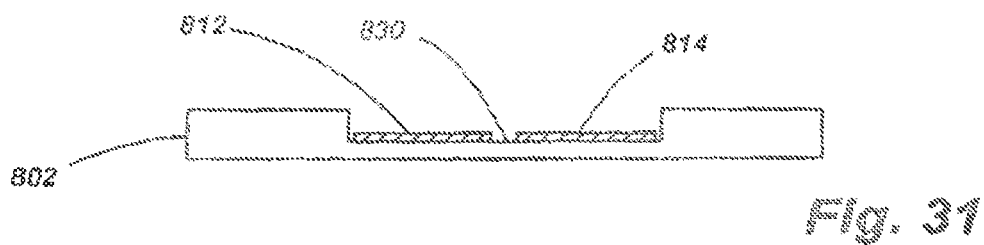
FIG. 31 is a schematic view showing a second step in the manufacturing process of the wireless pressure sensor of FIG. 29.
Figure 32:
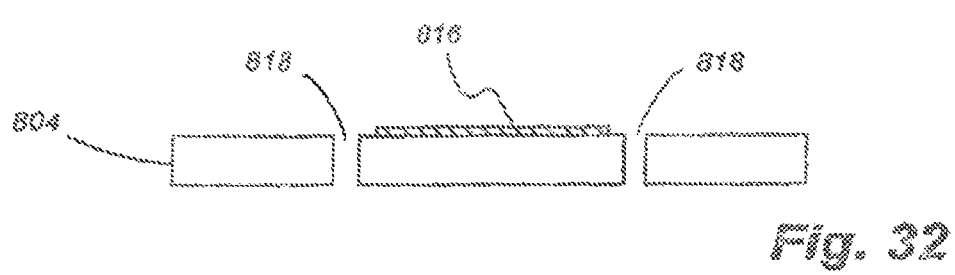
FIG. 32 is a schematic view showing a third step in the manufacturing process of the wireless pressure sensor of FIG. 29.

FIG. 30 illustrates a first step in the process for manufacturing the sensor 800. A recess 830 is formed in the upper surface of the bottom wafer. Then, as shown in FIG. 32, the plates 812, 814 are formed in the base of the recess 830. Referring to FIG. 32, the plate 816 is formed on the upper surface of the second wafer 804, and the through holes 818 are formed at the periphery of the plate 816. The second wafer is then inverted and stacked on top of the first wafer.

Thereafter, the coil 822 is positioned atop the second wafer, and electrical connections are made through the holes 818 to the lower plates 812, 814. After formation of the pressure sensitive, capacitor and inductor coil and connecting them together, hermetic encapsulation of the pressure sensitive cavity and inductor coil is performed. The third substrate wafer 806 is prepared with the deep recess 820, sufficient to contain the inductor coil 822. The recess 820 can be formed in a variety of ways, including laser rastering, glass machining, and ultrasonic machining. This third wafer 806 is bonded to the second wafer 804 and subsequently, the sensors are cut out using a laser to release the sensors from the wafer stack and form the hermetic seal in the process of the cut.

The sensors described above can be adapted for use within an organ or a lumen, depending upon what type of attachment or stabilizing means is employed. FIGS. 33-36 illustrate a sensor 1001 suitable for use within an organ such as the heart. The sensor 1001 has a generally cylindrical body 1002 that hermetically houses the capacitor and inductor elements previously described. The sensor 1001 further has a pressure sensitive surface 1003 (FIGS. 35 and 36) on one end of the cylindrical body 1002 and a screw-type anchoring device 1004 extending upward from the opposite end of the body.

FIGS. 33-41 illustrate a first embodiment of a delivery device 1000 (FIGS. 38, 40, and 41) for implanting a pressure sensor 1001 in a heart chamber. The sensor 1001 has a generally cylindrical body 1002 that houses the capacitor and inductor elements previously described. The sensor 1001 further has a pressure sensitive surface 1003 (FIGS. 35, 36, and 41) on one end of the cylindrical body 1002 and a screw-type anchoring device 1004 extending upward from the opposite end of the body. A retention mechanism 1005 of the delivery device 1000 comprises a "clamshell" housing 1006 wherein left and right housing halves 1008, 1010 are resiliently deformable with respect to one another, much in the manner of a clothespin. The housing 1006 has a recess 1012 (FIGS. 35 and 36) formed in its upper end, dimensioned to receive the sensor 1001 therewithin. A reverse-threaded bore 1014 is formed in the lower end of the housing 1006, and a smooth counterbore 1016 is formed in the lower end of the housing 1006 coaxially with the threaded bore 1014.

With further reference to the delivery device 1000, a screw 1018 has a reverse-threaded shaft 1019 and a screw head 1020. The screw head 1020 is mounted to the upper end of a dual-coil, flexible, torqueable shaft 1022. As can be seen at 1024 of FIG. 37, a portion of the outer coil 1026 is removed for purposes of illustration to show the inner coil 1028, which is counterwound with respect to the outer coil 1026.

The reverse-threaded screw 1018 threadably engages the reverse-threaded bore 1014 in the lower end of the retention mechanism 1005. As the screw head 1020 advances into the smooth counterbore 1016 in the base of the housing 1006, the lower ends of the two housing halves 1008, 1010 are spread apart. This causes the upper ends of the housing halves 1008, 1010 to close together, thereby grasping the sensor 1001.

Referring now to FIGS. 38-41, delivery of the sensor 1001 of the invention to a heart chamber may be accomplished as follows. The physician gains access into a vein that is suitable for access into the right ventricle using methods such as the Seldinger technique. Examples of these access sites would be the right jugular, left subclavian, or right femoral veins. A guidewire is advanced into the right ventricle. A large vessel introducer with an adjustable hemostatic valve is inserted over the guidewire and advanced until its tip is positioned in the right ventricle.

The sensor 1001 is mounted to the delivery device 1000 with the longitudinal axis of the device oriented normal to the pressure-sensitive surface of the sensor and with the anchor or stabilizer 1004 facing the distal end of the shaft 1022. The sensor anchor 1004 can be covered with a soluble, biocompatible material, or a thin, retractable diaphragm cover (not shown). The purpose of such covering is to conceal the anchoring mechanism or stabilizer 1004 and to protect the heart from inadvertent damage during sensor positioning prior to engaging the anchoring mechanism (which, in the case of the disclosed sensor 1001 is configured to engage the tissue of the septum). A torqueable, kink-resistant, shaped guiding catheter (not shown) can be loaded over the shaft 1022 of the delivery device in order to provide additional means for steering the sensor into position. The characteristics of this guiding catheter are that the outer diameter is small enough to fit within the introducer sheath, and the inner diameter is large enough to load over the shaft 1022 of the delivery device 1000.

Figure 38:
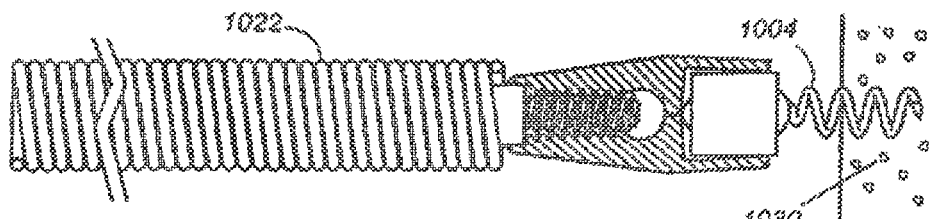
FIG. 38 is a side view of a delivery device comprising the retention mechanism of FIG. 33 and the shaft of FIG. 37, illustrating a first step in the delivery of a sensor into the wall of a septum.
Figure 39:
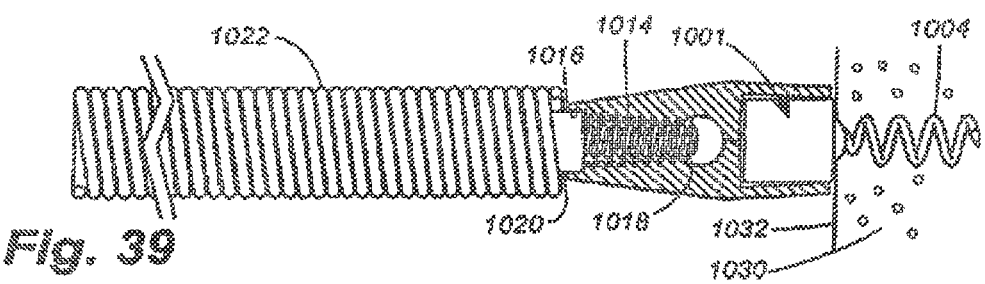
FIG. 39 is a side view of the delivery device of FIG. 38, illustrating a second step in the delivery of a sensor into the wall of a septum.
Figure 40:
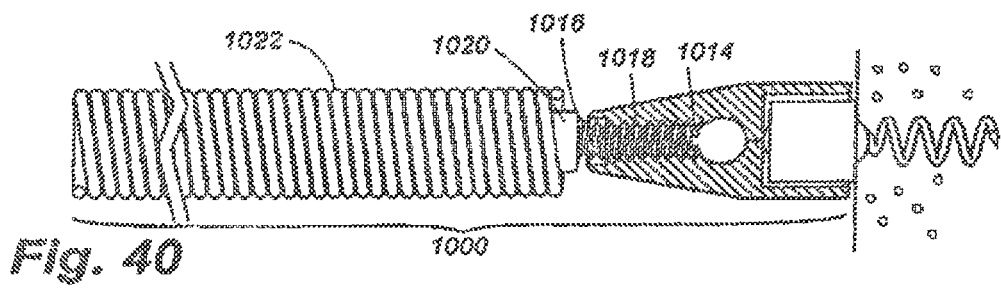
FIG. 40 is a side view of the delivery device of FIG. 38, illustrating a third step in the delivery of a sensor into the wall of a septum.
Figure 41:
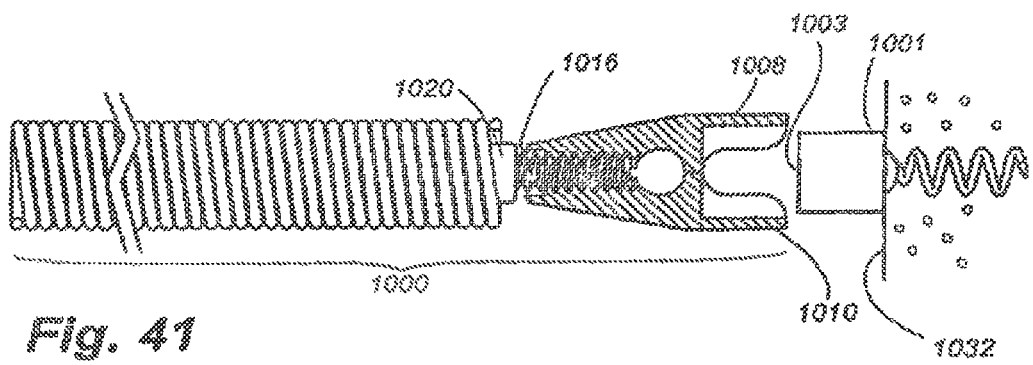
FIG. 41 is a side view of the delivery device of FIG. 38, illustrating a fourth step in the delivery of a sensor into the wall of a septum.

Referring to FIG. 38, the shaft 1022 of the delivery device 1000 is rotated in a clockwise direction to screw the anchor 1004 of the sensor into the tissue 1030 of the septum. When the anchor 1004 has been fully inserted into the tissue 1030, as shown in FIG. 39, the sensor 1001 tightens against the wall 1032 of the septum and creates a resistance. This resistance is sufficient to overcome the resistance between the reverse-threaded screw 1018 and the corresponding reverse-threaded bore 1014 in the housing 1006 of the retention mechanism 1005. Consequently, continued rotation of the shaft 1022 of the delivery device 1000 in the clockwise direction will withdraw the screw 1018 from its bore 1014, as illustrated in FIG. 40. Once the screw head 1020 has cleared the smooth counterbore 1016 in the lower end of the housing 1006 of the retention mechanism, the lower ends of the two housing halves 1008, 1010 return to their normal, closed configuration, thereby opening the upper ends of the two housing halves and releasing the sensor 1001, as depicted in FIG. 41. The delivery device 1000 is then withdrawn from the patient, leaving the sensor 1001 anchored to the wall 1032 of the septum with its pressure-sensing surface 1003 facing outward.

A feature of the disclosed embodiment is the use of a reverse-threaded screw 1018 and corresponding bore 1014 so that rotating the shaft 1022 in a normal "tightening" direction will first screw the sensor into the wall of the septum and then open the retention mechanism 1005 to release the sensor 1001, all without having to reverse direction of rotation of the shaft. To permit this arrangement, it is necessary that the screw 1018 engage the retention mechanism 1005 with enough mechanical force that the initial rotation of the shaft 1022 will cause the sensor to screw into the wall of the septum, rather than withdraw the screw 1018 from the retention mechanism 1005. In addition, it is also necessary that the screw be sufficiently loose with respect to the retention mechanism that once the sensor has completely screwed into the wall of the septum, the torque resistance will overcome the engagement between the screw and the retention mechanism rather than continue to rotate the sensor 1001. This feature can be accomplished, for example, by controlling the tolerances between the screw 1018 and the retention mechanism 1005, and by controlling the resilient force exerted by the housing 1006 against the head 1020 of the screw.

Figure 42:
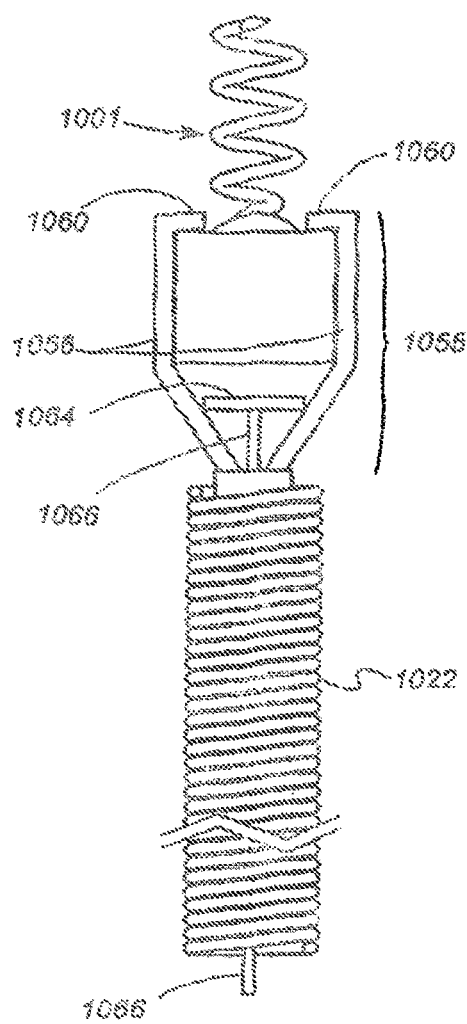
FIG. 42 is a side view of an alternate embodiment of a delivery device for delivering a sensor into the wall of a septum, with the retention mechanism of the delivery device in a closed configuration.
Figure 43:
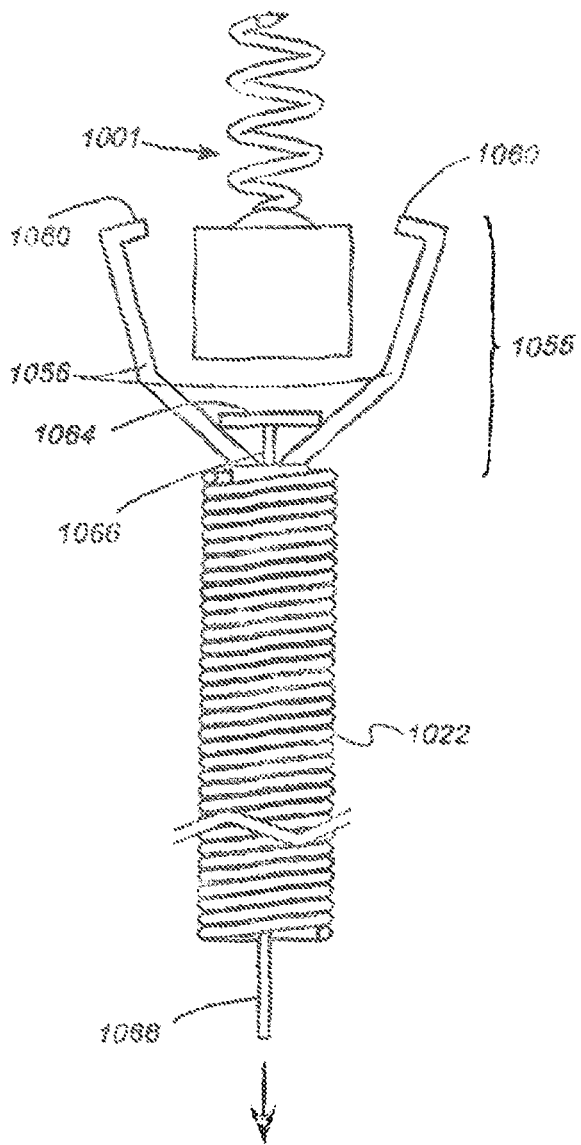
FIG. 43 is a side view of the delivery device of FIG. 42 showing the retention mechanism in an open configuration.

FIGS. 42 and 43 illustrate an alternate embodiment of a retention mechanism 1055. The retention mechanism 1055 is mounted to a flexible, torqueable shaft 1022, just as in the previously disclosed embodiment. However, rather than the clamshell housing 1006, the retention mechanism 1055 comprises a plurality of resilient wire fingers 1056 extending upward from a base 1058. The fingers 1056 of the disclosed embodiment are comprised of nitinol, though any suitable resilient biocompatible material can be used. Hooks 1060 at the upper ends of the wire fingers 1056 wrap around the upper edges of the body 1002 of the sensor 1001. In the disclosed embodiment there are four such wire fingers 1056 spaced 90° apart around the circumference of the cylindrical sensor body 1002, although a greater or lesser number of fingers 1056 can be used. Only two fingers 1056 are shown in the drawings for convenience of illustration.

A spreader 1064 is disposed between the fingers 1056. The spreader 1064 is attached to a pull-wire 1066, which extends through the longitudinal opening of the shaft 1022 and to a location outside of the patient. When the physician desires to release the retention mechanism 1055 from the sensor 1001, he simply exerts a tension on the pull-wire 1066. In response, the spreader moves downward and biases the fingers 1056 apart, releasing the sensor 1001 from the retention mechanism 1055. In the disclosed embodiment the spreader 1064 is a circular disk or a frustocone, but it will be understood that any shape can be used which biases the fingers apart in response to tension applied to the pull-wire 1066.

Figure 44:
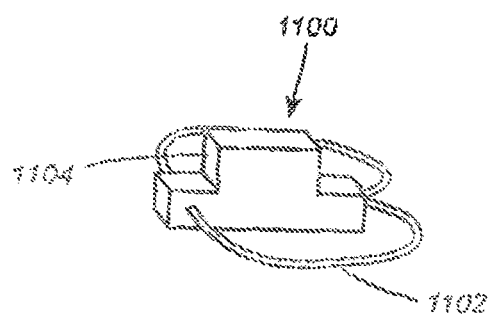
FIG. 44 is an isometric view of a sensor comprising an alternate arrangement for anchoring the sensor within a lumen of a patient.
Figure 45:
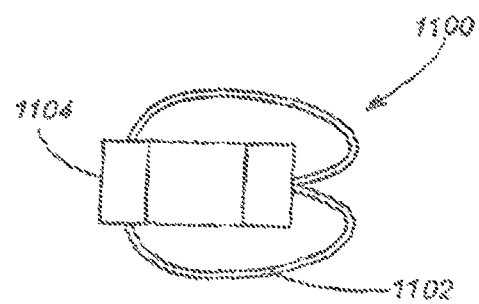
FIG. 45 is a top view of the sensor of FIG. 44.
Figure 46:
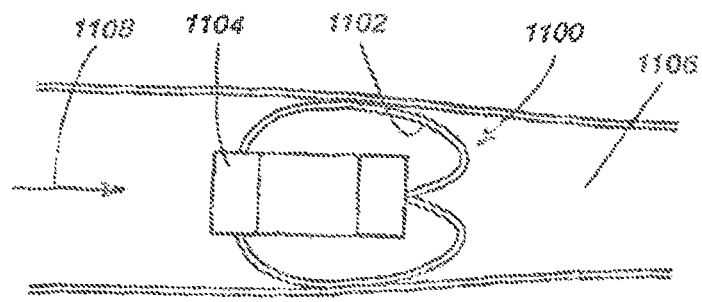
FIG. 46 is a top view showing the sensor of FIG. 44 lodged within a lumen.

By changing the anchoring means, the same basic sensor 1001 can be adapted for use within a lumen such as an artery or arteriole in the pulmonary artery vasculature. FIGS. 44-46 illustrate a sensor 1100 of the type described above. The sensor 1100 has a wire loop 1102 extending outward from the sensor body 1104. As shown in FIG. 46, the wire loop 1102 causes the sensor 1100 to lodge within a lumen 1106, with the sensor located centrally within the lumen and allowing blood flow all around in the direction indicated by the arrow 1108.

A delivery apparatus 1150 for securing, delivering and deploying an implant 1100 having an anchoring mechanism 1102 is shown in FIGS. 47-51. The various components of the delivery apparatus 1150 are shown individually in FIGS. 47-50. As shown in FIG. 47, the delivery apparatus includes an elongated shaft 1152 having proximal and distal ends 1153, 1154 respectively. The shaft 1152 has a main lumen 1155, which extends the length of the shaft. A port 1156 places the main lumen 1155 in communication with the ambient at an Intermediate location along the shaft 1152. A secondary lumen 1157 includes a proximal portion 1158 and a distal portion 1159. The proximal portion 1158 extends along a partial length of the shaft 1152 and terminates in a port 1160 in the sidewall of the shaft. The distal portion 1159 originates in a port 1161 in the sidewall of the shaft and extends in a distal direction to an end 1162.

A tether wire, 1163 shown in FIG. 48, 1*s* adapted to be slidably positioned within the secondary lumen 1157 of the shaft 1152.

A core wire 1164, shown in FIG. 49, is configured to be received within the main lumen 1155 of the shaft 1152 and provides stiffness to the delivery apparatus 1150. The core wire 1164 has a decreasing diameter toward its distal end 1165, providing an increased flexibility in the distal end of the delivery apparatus 1150. The core wire 1164 is fixed in the main lumen 1155 of the shaft 1152 using adhesive, thermocompression, or any other suitable fixation means.

Referring to FIG. 50, a conventional guide wire 1166 is dimensioned to extend beyond the distal end 1154 of the shaft 1152 and to be received within a distal portion of the main lumen 1155 of the shaft.

FIG. 51 shows the delivery apparatus 1150 with sensor 1100 mounted. The core wire 1164 is disposed within the main lumen 1155 of the shaft 1152. The tether wire 1163 extends through the proximal portion 1158 of the secondary lumen 1157 of the shaft 1152 and exits through the port 1160 in the shaft sidewall. The tether wire 1163 then is threaded through the body 1104 of the sensor 1100 and passed into the port 1161 and hence into the distal portion 1159 of the secondary lumen 1157. The guidewire 1166 extends along-side the proximal portion of the shaft 1152 and enters the main lumen 1155 of the shaft 1152 at the port 1156. The guidewire 1166 then passes through the distal portion of the main lumen 1155 and exits the distal end 1154 of the shaft 1152.

A vessel introducer is placed in an access site such as the right internal jugular vein, the subclavian artery, the right femoral vein, or any other suitable access site. The guidewire 1164 is inserted through the vessel introducer and guided to the target site using suitable medical imaging technology. The delivery apparatus 1150 with sensor 1100 mounted thereto is then threaded over the guidewire and inserted into the vessel introducer.

After the delivery apparatus is in the vessel introducer, the apparatus is navigated over the guidewire to a deployment site in the pulmonary artery. The implant 1100 is deployed by pulling the tether wire 1160 proximally to disengage the implant from the shaft 1152. The delivery apparatus and guidewire are then removed from the body.

The implant 1100 may then "float" through the narrowing pulmonary artery vasculature until it reaches a location at which the vessel is sufficiently narrow that the implant lodges within the vessel, as shown in FIG. 46. At that point the implant will be firmly anchored within the vasculature.

In alternate embodiments (not shown), the secondary lumen 1157 of the introducer 1150 can comprise a single, uninterrupted lumen having two ports 1160, 1161, rather than two separate lumen portions 1158, 1159. In addition, the secondary lumen 1157 can extend all the way through the distal end 1154 of the shaft 1152, rather than terminating at an end 1160 short of the distal end of the shaft.

Finally, it will be understood that the preferred embodiment has been disclosed by way of example, and that other modifications may occur to those skilled in the art without departing from the scope and spirit of the appended claims.

What is claimed is:

1. An implantable wireless sensor for determining a physical property of a medium comprising:
    an upper wafer formed from a dielectric material, the upper wafer having one or more channels;
    a first capacitor plate and a second capacitor plate formed on a lower surface of the upper wafer;
    an inductor formed from one or more windings of a conductive material, the inductor being contained within the one or more channels in the upper wafer in fixed relation to the first and second capacitor plates, the inductor comprising first and second inductor leads, the first lead being electrically coupled to the first capacitor plate and the second lead electrically coupled to the second capacitor plate;
    a lower wafer formed from the dielectric material, the lower wafer being thinner than the upper wafer; and
    a third capacitor plate formed on an inner surface of the lower wafer, the upper and lower wafers being fused together to form a monolithic housing such that the first and second capacitor plates are arranged in parallel, spaced-apart relation from the third capacitor plate to form a capacitor, a portion of the lower wafer comprising a pressure sensitive deflective region underlying at least a portion of the third capacitor plate, whereby the deflective region deflects in response to changes in ambient pressure in the medium altering the spacing between the first and second capacitor plates and the third capacitor plate.

2. The sensor of claim 1, wherein the inductor is immobilized with respect to at least said first capacitor plate.

3. The sensor of claim 1 wherein the inductor comprises wire of sufficient strength so the inductor does not shift position relative to the capacitor plates.

4. The sensor of claim 1, wherein the inductor comprises a coil formed on a bobbin.

5. The sensor of claim 4, where the bobbin is comprised of a thermoplastic material and heated to encapsulate and/or adhere to a surface of a coil receiving trench.

6. The sensor of claim 4, where the bobbin is press fit to at least one surface of the one or more channels in the upper wafer.

7. The sensor of claim 1, where the inductor comprises use a thermosetting or thermoplastic material applied to a pre-formed coil to impart additional stability to the coil.

8. The sensor of claim 7, further comprising a thermosetting polymer applied to at least one space between the inductor and the one or more channels in the upper wafer, wherein the polymer is applied in liquid form and cured.

9. The sensor of claim 1, wherein the upper and lower wafers comprise an electrically insulating selected from the group consisting of fused silica, quartz, Pyrex, and sintered zirconia.

10. The sensor of claim 1, wherein the first and second capacitor plates are spaced apart from the third capacitor plate by a distance of from 0.1 to 10 micrometers.

11. The sensor of claim 1 wherein the upper wafer comprises an upper wafer recess and wherein the first and second capacitor plates are formed in the upper wafer recess.

12. The sensor of claim 11 wherein the first and second capacitor plates are electroplated in the upper wafer recess.

13. The sensor of claim 11 wherein the height of the first and second capacitor plates is less than or equal to a depth of the upper wafer recess.

14. The sensor of claim 1 wherein the inductor and capacitor comprise an inductive-capacitive (LC) resonant circuit, and wherein a resonant frequency of the LC resonant circuit varies in response to changes in ambient pressure in the medium.

* * * * *